(12) United States Patent
Vic et al.

(10) Patent No.: US 11,369,559 B2
(45) Date of Patent: Jun. 28, 2022

(54) PROCESS FOR TREATING KERATIN SUBSTANCES USING A COMPOSITION COMPRISING A MODIFIED PHOTO-DIMERIZABLE POLYMER

(71) Applicant: L'OREAL, Paris (FR)

(72) Inventors: Gabin Vic, Saint-Ouen (FR); Eric Parris, Saint-Ouen (FR); Frédéric Woodland, Saint-Ouen (FR)

(73) Assignee: L'OREAL, Paris (FR)

( * ) Notice: Subject to any disclaimer, the term of this patent is extended or adjusted under 35 U.S.C. 154(b) by 616 days.

(21) Appl. No.: 16/064,485

(22) PCT Filed: Dec. 20, 2016

(86) PCT No.: PCT/EP2016/081892
§ 371 (c)(1),
(2) Date: Jun. 21, 2018

(87) PCT Pub. No.: WO2017/108767
PCT Pub. Date: Jun. 29, 2017

(65) Prior Publication Data
US 2019/0000743 A1    Jan. 3, 2019

(30) Foreign Application Priority Data
Dec. 23, 2015 (FR) ..................... 1563288

(51) Int. Cl.
| A61Q 5/06 | (2006.01) |
| A61K 8/81 | (2006.01) |
| A61Q 5/04 | (2006.01) |
| A61K 8/06 | (2006.01) |

(52) U.S. Cl.
CPC .............. *A61K 8/8135* (2013.01); *A61K 8/06* (2013.01); *A61Q 5/04* (2013.01); *A61Q 5/06* (2013.01); *A61K 2800/81* (2013.01); *A61K 2800/95* (2013.01); *A61Q 5/065* (2013.01)

(58) Field of Classification Search
None
See application file for complete search history.

(56) References Cited

U.S. PATENT DOCUMENTS

| 2,811,510 | A | 10/1957 | Leubner et al. |
| 3,177,119 | A | 4/1965 | Zoebelein |
| 4,137,180 | A | 1/1979 | Naik et al. |
| 4,874,554 | A | 10/1989 | Lange et al. |
| 5,061,603 | A | 10/1991 | Hamilton et al. |
| 5,300,285 | A | 4/1994 | Halloran et al. |
| 5,618,523 | A | 4/1997 | Zysman et al. |
| 2006/0239946 | A1 | 10/2006 | Samain et al. |
| 2007/0112094 | A1 | 5/2007 | Noutary |
| 2011/0259355 | A1 | 10/2011 | Ybarra et al. |

FOREIGN PATENT DOCUMENTS

| EP | 0092901 A2 | 11/1983 |
| EP | 0313220 A2 | 4/1989 |
| EP | 0313221 A2 | 4/1989 |
| EP | 1058154 A1 | 12/2000 |
| EP | 1572139 A1 | 9/2005 |
| FR | 2673179 A1 | 8/1992 |
| GB | 2030575 A | 4/1980 |
| GB | 2076826 A | 12/1981 |
| JP | 11-073305 A | 3/1999 |
| JP | 2012-500210 A | 1/2012 |
| WO | 96/29312 A1 | 9/1996 |

OTHER PUBLICATIONS

Noll, Walter, "Chemistry and Technology of Silicones," Academic Press, New York, San Francisco, London, 1968, pp. 1-23.
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
Wertz, et al., Essential Fatty Acids and Epidermal Integrity, Archive of Dermatology, vol. 123, Oct. 1987, pp. 1381-1384.
International Search Report from International Searching Authority for International Patent Application No. PCT/EP2016/081892, dated Mar. 17, 2017, 3 pages.
Japanese Office Action for counterpart Application No. 2018-532643, dated May 27, 2019 (with translation).
Hasegawa, Masaki, "Photopolymerization of Diolefin Crystals," Chemical Reviews, vol. 83, No. 5, Oct. 1983, pp. 507-518.
Ichimura et al., Preparation and Characteristics of Photocrosslinkable Poly(vinyl Alcohol), Journal of Polymer Science: Polymer Chemistry Edition, Wiley & Sons, vol. 20, (1982), pp. 1419-1432.
Marck, J., "Reactions", Advanced Organic Chemistry, 4th Edition, Wiley Interscience, NY, 1992, p. 855.
Roth et al., "DMI-Photopolymers and Their Technical Application," Polymers Paint Colour Journal, vol. 178, 1988, p. 209-212.
Uhlich et al., "Synthesis of a hydrophobised and photocrosslinkable prepolymer based on poly(vinyl alcohol)," Reactive & Functional Polymers, 28, (1995), pp. 55-60.

*Primary Examiner* — Jyothsna A Venkat
(74) *Attorney, Agent, or Firm* — The Marbury Law Group, PLLC

(57) ABSTRACT

The present invention relates to a general process for treating keratin substances, preferably keratin fibres, comprising the following steps: c) applying to the keratin substances a composition comprising at least one photo-crosslinkable polymer including at least one photo-dimerizable pendant group and at least one hydrophobic pendant group, and d) irradiating said composition on the keratin substances to crosslink the polymer.

12 Claims, No Drawings

PROCESS FOR TREATING KERATIN SUBSTANCES USING A COMPOSITION COMPRISING A MODIFIED PHOTO-DIMERIZABLE POLYMER

CROSS REFERENCE TO RELATED APPLICATIONS

This is a national stage application of PCT/EP2016/081892, filed internationally on Dec. 20, 2016, which claims priority to French Application No. 1563288, filed on Dec. 23, 2015, both of which are incorporated by reference herein in their entireties.

The present invention relates to a process for treating keratin substances, such as keratin fibres and particularly hair, with a composition comprising at least one modified photo-crosslinkable polymer. Such a composition can produce a sleeve that is resistant to washing.

It is known for the person skilled in the art to use photo-crosslinkable materials such as materials from vinyl monomers, and especially (meth)acrylate monomers.

Accordingly, U.S. Pat. No. 5,300,285 describes a process for waving hair and a composition for using this process, and especially a silicone-based neutralizing composition, including a silicone with a vinyl function, a free-radical photoinitiator and a solvent. This composition acts as a substitute for neutralizing solutions based on hydrogen peroxide when it is applied to hair after a permanent deformation process of the hair and photo-crosslinking of the composition. This composition has the advantage of functioning simultaneously as a crosslinking agent for keratin, while giving hair advantages such as conditioning and a soft feel. Photo-crosslinking is triggered in the composition by the photoinitiator (generally an acetophenone derivative), which releases a substituent when exposed to radiation in the UVA domain especially between 250 and 400 nm, preferably 350-385 nm, such as 365 nm.

Unfortunately, photo-polymerization of the silicone with a vinyl function in the presence of a photoinitiator leads to irreversible silicone photo-crosslinking with a vinyl function. In other words, once it is photo-crosslinked, the deposit cannot be easily and at any moment removed from the hair.

Japanese patent JP 09249812 describes interpenetrating networks containing molecules forming chelates and uses thereof, and more particularly compositions containing partially saponified polyvinyl acetate polymers with stilbazolium groups, crosslinked and containing chelating agents. This previously crosslinked material can then be used as is in medical or cosmetic applications. However, no mention is made in this document of application to hair before irradiation.

Document EP1572139 describes a photo-dimerizable composition that can make a deposit on keratin substances, particularly hair. This document teaches that such deposits allow a long-lasting deposit to be obtained that provides durable cosmetic properties over time that are easily removed. The deposits obtained from crosslinkable compounds described in this document do however have limited persistence. Moreover, these compounds are not deposited uniformly on the hair and the deposit depends greatly on the amount of hair damage. Accordingly, the result is not uniform between the hair's roots and tips.

The present invention therefore relates to providing a treatment process for keratin substances from a composition comprising a photo-crosslinkable polymer that does not present the drawbacks of the compositions of the state of the art. The goal of the invention is especially to develop photo-dimerizable compositions that resist washing, allow a uniform deposit on all of the hair, on natural hair and on damaged hair.

Accordingly, the present invention relates to a treatment process for keratin substances comprising the application of a composition comprising at least one photo-crosslinkable polymer including at least one pendant photo-dimerizable group and at least one hydrophobic pendant group and one step of irradiating the composition on the keratin substances to crosslink the composition.

For the purposes of the present invention and unless otherwise indicated:

an "alkylene chain" represents an acyclic $C_1$-$C_{20}$ divalent hydrocarbon chain, particularly a $C_1$-$C_6$ chain, more particularly a $C_1$-$C_2$ chain when the chain is linear, optionally substituted with one or more groups, which may be identical or different, chosen from i) hydroxyl, ii) ($C_1$-$C_2$)alkoxy, iii) (poly)hydroxy($C_2$-$C_4$)alkoxy(di) ($C_1$-$C_2$)(alkyl)amino, iv) $R^a$—$Z^a$—$C(Z^b)$—$Z^o$—, and v) $R^a$—$Z^a$—$S(O)_t$—$Z^c$— with $Z^a$ and $Z^b$, which may be identical or different, representing an oxygen or sulfur atom, or a group $NR^{a'}$; $Z^c$, representing a bond, an oxygen or sulfur atom, or a group $NR^a$; $R^a$, representing an alkali metal, a hydrogen atom, an alkyl group, or alternatively is absent if another part of the cationic molecule and $R^{a'}$ representing a hydrogen atom or an alkyl group; more particularly, the groups iv) are chosen from carboxylate —C(O)O⁻ or —C(O) OMetal (Metal=alkali metal), carboxyl —C(O)—OH, guanidino $H_2H$—$C(NH_2)$—NH—, amidino $H_2H$—C ($NH_2$)—, (thio)ureo $H_2N$—C(O)—NH— and $H_2N$—C(S)—NH—, aminocarbonyl —C(O)—$NRa'_2$ or aminothiocarbonyl —C(S)—$NRa'_2$; carbamoyl Ra'—C (O)—NRa'— or thiocarbamoyl Ra'—C(S)—NRa'— with Ra', which may be identical or different, representing a hydrogen atom or a ($C_1$-$C_4$)alkyl group;

the "aryl" or "heteroaryl" substituents or the aryl or heteroaryl part of a substituent may be substituted with at least one substituent borne by a carbon atom, chosen from:

a $C_1$-$C_{16}$ and preferably $C_1$-$C_8$ alkyl substituent, optionally substituted with one or more substituents chosen from the substituents hydroxyl, $C_1$-$C_2$ alkoxy, $C_2$-$C_4$ (poly)hydroxyalkoxy, acylamino, amino substituted with two $C_1$-$C_4$ alkyl substituents, which may be identical or different, optionally bearing at least one hydroxyl group, or the two substituents possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;

a halogen atom;

a hydroxyl group;

a $C_1$-$C_2$ alkoxy substituent;

a $C_2$-$C_4$ (poly)hydroxyalkoxy substituent;

an amino substituent;

a 5- or 6-membered heterocycloalkyl substituent;

an optionally cationic 5- or 6-membered heteroaryl substituent, preferentially imidazolium, optionally substituted with a ($C_1$-$C_4$)alkyl substituent, preferentially methyl;

an amino substituent substituted with one or two identical or different $C_1$-$C_6$ alkyl substituents, optionally bearing at least:

i) one hydroxyl group,
ii) one amino group optionally substituted with one or two optionally substituted $C_1$-$C_3$ alkyl substituents, said alkyl substituents possibly forming with the nitrogen atom to which they are attached a saturated or unsaturated, optionally substituted 5- to 7-membered heterocycle, optionally comprising at least one other nitrogen or non-nitrogen heteroatom,
iii) one quaternary ammonium group —$N^+R'R''R'''$, $M^-$ for which R', R" and R'", which may be identical or different, represent a hydrogen atom or a $C_1$-$C_4$ alkyl group; and $M^-$ represents the counterion of the organic or inorganic acid or of the corresponding halide;
iv) or one optionally cationic 5- or 6-membered heteroaryl substituent, preferentially imidazolium, optionally substituted with a ($C_1$-$C_4$)alkyl substituent, preferentially methyl;
  an acylamino substituent (—NR—C(O)—R') in which the R substituent is a hydrogen atom or a $C_1$-$C_4$ alkyl substituent optionally bearing at least one hydroxyl group and the R' substituent is a $C_1$-$C_2$ alkyl substituent;
  a carbamoyl substituent ((R)$_2$N—C(O)—) in which the R substituents, which may be identical or different, represent a hydrogen atom or a $C_1$-$C_4$ alkyl substituent optionally bearing at least one hydroxyl group;
  an alkylsulfonylamino substituent (R'—S(O)$_2$—N(R)—) in which the R substituent represents a hydrogen atom or a $C_1$-$C_4$ alkyl substituent optionally bearing at least one hydroxyl group and the R' substituent represents a $C_1$-$C_4$ alkyl substituent or a phenyl substituent; an aminosulfonyl substituent ((R)$_2$N—S(O)$_2$—) in which the R substituents, which may be identical or different, represent a hydrogen atom or a $C_1$-$C_4$ alkyl substituent optionally bearing at least one hydroxyl group,
  a carboxyl substituent in the acid or salt form (preferably salified with an alkali metal or a substituted or unsubstituted ammonium);
  a cyano group;
  a nitro or nitroso group;
  a polyhaloalkyl group, preferentially the trifluoromethyl group;
  the cyclic, cycloalkyl or heterocyclic part of a non-aromatic substituent may be substituted with at least one substituent chosen from the following groups:
    hydroxyl;
    $C_1$-$C_4$ alkoxy or $C_2$-$C_4$ (poly)hydroxyalkoxy;
    $C_1$-$C_4$ alkyl;
    alkylcarbonylamino (R—C(O)—N(R')—) in which the R' substituent is a hydrogen atom or a $C_1$-$C_4$ alkyl substituent optionally carrying at least one hydroxyl group and the R substituent is a $C_1$-$C_2$ alkyl substituent or an amino substituent optionally substituted by one or two identical or different $C_1$-$C_4$ alkyl groups, themselves optionally carrying at least one hydroxyl group, said alkyl substituents possibly forming, with the nitrogen atom to which they are attached, a saturated or unsaturated and optionally substituted 5- to 7-membered heterocycle, optionally comprising at least one other nitrogen or non-nitrogen heteroatom;
    alkylcarbonyloxy (R—C(O)—O—) in which the R substituent is a $C_1$-$C_4$ alkyl substituent or an amino group optionally substituted by one or two identical or different $C_1$-$C_4$ alkyl groups, themselves optionally bearing at least one hydroxyl group, where said alkyl substituents may form, with the nitrogen atom to which they are attached, a saturated or unsaturated and optionally substituted 5- to 7-membered heterocycle optionally comprising at least one other nitrogen or non-nitrogen heteroatom;
  alkoxycarbonyl (R-G-C(O)—) in which the R substituent is a $C_1$-$C_4$ alkoxy substituent, G is an oxygen atom or an amino group optionally substituted with a $C_1$-$C_4$ alkyl group optionally bearing at least one hydroxyl group, where said alkyl substituent may form with the nitrogen atom to which it is attached a saturated or unsaturated, optionally substituted 5- to 7-membered heterocycle, optionally comprising at least one other nitrogen or non-nitrogen heteroatom;
  a cyclic, cycloalkyl or heterocyclic substituent, or a non-aromatic part of an aryl or heteroaryl substituent, which may also be substituted with one or more oxo groups;
  a cycloalkyl substituent is a mono- or bicyclic, hydrocarbon substituent comprising 3 to 10 carbon atoms, preferably 4 to 7 carbon atoms, such as cyclopentyl or cyclohexyl;
  a hydrocarbon-based chain is unsaturated when it includes one or more double bonds and/or one or more triple bonds;
  an "aryl" substituent represents a monocyclic or fused or non-fused polycyclic carbon-based group comprising from 6 to 22 carbon atoms, and in which at least one ring is aromatic; preferentially, the aryl substituent is a phenyl, biphenyl, naphthyl, indenyl, anthracenyl or tetrahydronaphthyl;
  a "heteroaryl substituent" represents an optionally cationic, 5- to 22-membered, monocyclic or fused or non-fused polycyclic group, comprising from 1 to 6 heteroatoms chosen from nitrogen, oxygen, sulfur and selenium, at least one ring of which is aromatic; preferentially, a heteroaryl substituent is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof;
  a "heterocyclic substituent" is a 5- to 22-membered monocyclic or fused or non-fused polycyclic substituent which may contain one or two unsaturations but is non-aromatic, comprising from 1 to 6 heteroatoms chosen from nitrogen, oxygen, sulfur and selenium atoms;
  a "heterocycloalkyl substituent" is a heterocyclic substituent comprising at least one saturated ring;
  a "cationic heteroaryl substituent" is a heteroaryl group as defined above that includes an endocyclic or exocyclic quaternized cationic group,
  when the cationic charge is endocyclic, it is included in the electron delocalization via the mesomeric effect; for example, it is a pyridinium, imidazolium or indolinium group;

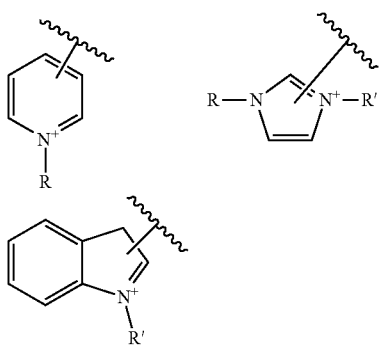

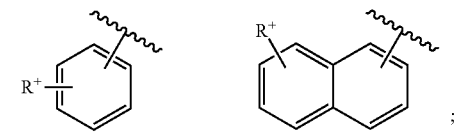

with R and R' being a heteroaryl substituent as defined above and particularly a (hydroxy)($C_1$-$C_8$)alkyl group such as methyl;

when the cationic charge is exocyclic, it is, for example, an ammonium or phosphonium substituent, such as trimethylammonium, which is outside the heteroaryl, such as pyridinyl, indolyl, imidazolyl or naphthalimidyl, in question:

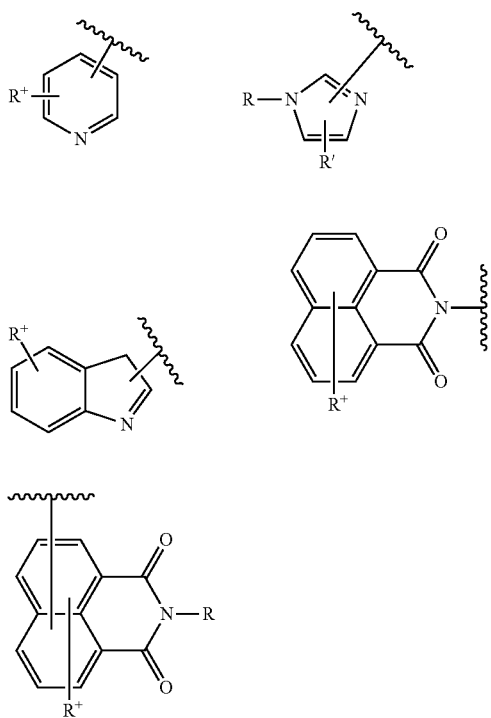

with R a heteroaryl substituent as defined above and $R^+$ an ammonium $R_aR_bR_cN^+$—, phosphonium $R_aR_bR_cP^+$— or ammonium $R_aR_bR_cN^+$—($C_1$-$C_6$)alkylamino group with $R_a$, $R_b$ and $R_c$, which may be identical or different, representing a hydrogen atom or a ($C_1$-$C_8$)alkyl group such as methyl;

a "cationic aryl carrying an exocyclic charge" means an aryl ring whose quaternized cationic group is outside said ring; it is especially an ammonium or phosphonium $R^+$ substituent, such as trimethylammonium, which is outside the aryl, such as phenyl or naphthyl:

an "alkyl substituent" is a linear or branched $C_1$-$C_{20}$ and preferably $C_1$-$C_8$ hydrocarbon-based substituent;

an "alkenylene substituent" is an unsaturated hydrocarbon-based divalent substituent as defined previously, which may contain from 1 to 4 conjugated or unconjugated double bonds —C=C—; the alkenylene group particularly contains 1 or 2 unsaturations;

the term "optionally substituted" applied to the alkyl substituent means that said alkyl substituent may be substituted with one or more substituents chosen from the following substituents: i) hydroxyl, ii) $C_1$-$C_4$ alkoxy, iii) acylamino, iv) amino optionally substituted with one or two identical or different $C_1$-$C_4$ alkyl substituents, where said alkyl substituents may form with the nitrogen atom that bears them a 5- to 7-membered heterocycle, optionally comprising one other nitrogen or non-nitrogen heteroatom; v) or a quaternary ammonium group —$N^+R'R''R'''$, $M^-$ for which R', R'' and R''', which may be identical or different, represent a hydrogen atom or a $C_1$-$C_4$ alkyl group, or else —$N^+R'R''R'''$ forms a heteroaryl such as imidazolium optionally substituted with a $C_1$-$C_4$ alkyl group, and $M^-$ represents the counterion of the corresponding organic acid, inorganic acid or halide;

an "alkoxy substituent" is an alkyloxy substituent for which the alkyl substituent is a linear or branched $C_1$-$C_{16}$ and preferentially $C_1$-$C_8$ hydrocarbon-based substituent; when the alkoxy group is optionally substituted, this implies that the alkyl group is optionally substituted as defined above;

"organic or inorganic acid salt" more particularly means the salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$; and xv) tetrafluoroboric acid $HBF_4$;

"Anionic counterion" is intended to mean an anion or an anionic group derived from an organic or inorganic acid salt which counterbalances the cationic charge of the colorant; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methanesulfonate or mesylate and ethanesulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii)

aryloxy sulfates: Ar—O—S(O)$_2$O$^-$, xiii) phosphates O=P(OH)$_2$—O$^-$, O=P(O$^-$)$_2$—OH O=P(O$^-$)$_3$, HO—[P(O)(O$^-$)]$_w$—P(O)(O$^-$)$_2$ with w being an integer; xiv) acetate; xv) triflate; and xvi) borates such as tetrafluoroborate, xvii) disulfate (O=)$_2$S(O$^-$)$_2$ or SO$_4^{2-}$ and monosulfate HSO$_4^-$;

the anionic counterion, derived from an organic or inorganic acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, polymers that comprise two cationic entities may contain either two "singly charged" anionic counterions or one "doubly charged" anionic counterion such as (O=)$_2$S(O$^-$)$_2$ or O=P(O$^-$)$_2$—OH;

moreover, the addition salts that may be used in the context of the invention are especially chosen from addition salts with a cosmetically acceptable base such as alkaline agents as defined below, for instance alkali metal hydroxides, such as sodium hydroxide or potassium hydroxide, aqueous ammonia, amines or alkanolamines;

the expression "at least one" is equivalent to "one or more"; and the expression "inclusive" for a range of concentrations means that the limits of the range are included in the defined range;

the term "photo-dimerizable group" means a chemical group that leads to photo-dimerization reactions under irradiation. For the purposes of the invention, photo-dimerization is a chemical reaction between two double bonds (of 2+2 type) or two pairs of double bonds (of 4+4 type), and more particularly between two double bonds (of 2+2 type);

The case of a reaction between two double bonds may be represented schematically in the following manner:

These photo-dimerization reactions are defined in the book Advanced Organic Chemistry, J. Marck, 4th edition, Wiley Interscience, N Y 1992, page 855.

Thus, the double bond, when it is photo-stimulated, generally when it is subjected to specific UV radiation, proves to be capable of reacting with another double bond by cyclization.

The double bond is called "activated", i.e. it is spontaneously photo-dimerizable, without requiring the presence of a photoinitiator or a chemical initiator.

This double bond is generally activated by the presence of an electron-attracting substituent (or electro-withdrawing substituent) in the alpha position of this photo-dimerizable double bond. As electron-attracting substituent mention may be made of aromatic rings such as the phenyl group optionally substituted by one or more halogen atoms, or electron-attracting groups such as NO$_2$, CN, R'—C(Y')—Y—, R'—Y—C(Y')—Y—, —S(O)$_2$—Y—R', where R' represents a hydrogen atom or a (C$_1$-C$_4$)alkyl group optionally substituted by one or more halogen atoms, where Y and Y', identical or different, represent an oxygen or sulfur atom or NR" where R" represents a hydrogen atom or a (C$_1$-C$_6$)alkyl group.

the term "Photoinitiator" is understood in the sense of the present invention as a compound that initiates the photo-dimerization reaction and releases a radical when irradiated, especially in the UV domain.

The process according to the invention comprises a step a) of applying a composition comprising a polymer including at least one i) photo-dimerizable pendant group and at least one ii) hydrophobic pendant group.

Preferably, the photo-dimerizable pendant groups i) that may be used according to the invention are chosen from monovalent substituents having the following formulae (I) and (II):

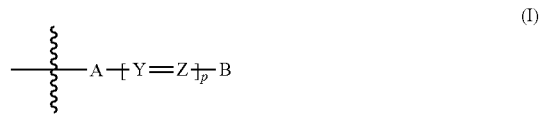

and the geometric isomers thereof, in which formulae (I) and (II):

Y and Z independently denote a nitrogen atom or a group C(R) where R represents a hydrogen atom or a (C$_1$-C$_4$)alkyl group such as methyl;

A represents one bond or a divalent group chosen from (C$_1$-C$_8$)alkylene, arylene, heteroarylene, cycloalkylene, heterocycloalkylene, (thio)carbonyl, (C$_2$-C$_8$) alkenylene substituents and combinations thereof;

B represents a monovalent group chosen from (C$_1$-C$_8$) alkyl substituents, aryl, optionally cationic heteroaryl, cycloalkyl, optionally cationic heterocycloalkyl, (thio) carbonyl, (C$_2$-C$_8$)alkenyl substituents and combinations thereof;

X represents a divalent group chosen from (C$_2$-C$_8$)alkylene, arylene, heteroarylene, cycloalkylene, heterocycloalkylene, (thio)carbonyl, (C$_2$-C$_8$)alkenylene substituents and combinations thereof;

p represents an integer between 1 and 5 inclusive, more particularly between 1 and 3, preferably p is 1;

represents the bond that connects the part of the monovalent substituent to the rest of the molecule;

and where each of the groups cited can optionally be substituted by one or more halogen atoms or groups chosen from (C$_1$-C$_6$)alkyl, hydroxy, amino, (di)(C$_1$-C$_6$)alkylamino, phenyl, carboxy, (C$_1$-C$_6$)alkoxy, (C$_1$-C$_6$) alkoxy(thio)carbonyl, hydrogen(thio)-carbonyl, sulfonato R—O—S(O)$_2$— or R—S(O)$_2$—O—, amide RR'N—C(O)— or R—C(O)—N(R')— or acyl R—C(O)—, ammonium RR'R"N+— groups, where R, R', and R", identical or different, represent a hydrogen atom or a $(C_1-C_4)$alkyl group.

The pendant dimerizable groups according to the invention are especially those cited in U.S. Pat. No. 2,811,510, EP 0 313 220, EP 0 313 221, EP 092 901, GB 2 030 575 and GB 2 076 826, and in articles "Chemical Review Vol 83, 5 1983, p 507" "Polym, Paint Colour Journal 1988, 178, p 209" and "Current Trends in Polymer Photochemistry, Ellis Morwood edition, NY, 1995".

As examples, photo-dimerizable pendant groups i) chosen from monovalent substituents from the following components may more particularly be cited:
  stilbene,
  styrylpyridinium (stilbazolium) having formula and the geometric isomers thereof:

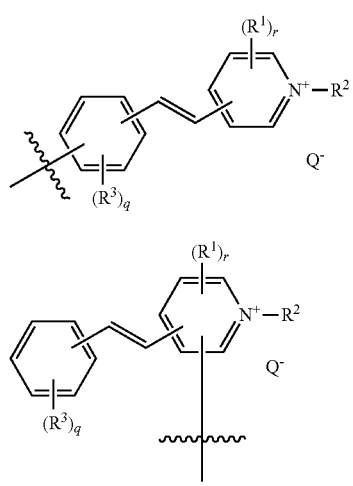

where:
  $R^1$ and $R^3$, identical or different, represent a halogen atom or a $(C_1-C_6)$alkyl group; or then two contiguous $R^1$ or $R^3$ groups together form with the carbon atoms that bear them, a benzo group;
  $R^2$ represents a hydrogen atom, a $(C_1-C_6)$alkyl group optionally substituted by one or more halogen atoms such as chlorine or hydroxy, preferably $R^2$ represents a $(C_1-C_6)$alkyl group such as methyl, ethyl, propyl;
  q and r represent an integer between 0 and 4 inclusive; and
  $Q^-$ represents an anionic counterion preferably chosen from halide ions such as chlorides, bromides, iodides, perchlorates, tetrafluoroborates, methylsulfate, phosphates, sulfates, methanesulfonates, p-toluenesulfonate;

represents the bond that connects the part of the monovalent substituent to the rest of the molecule being understood that the pendant group $A_2$ may be connected to the rest of the molecule via $R^2$;

preferably the

bond is found on the phenyl in the para position of the styryl group on $A_1$ or connected to the rest of the molecule via $R^2$ on $A_2$; preferentially the styryl group of $A_1$ and $A_2$ is found in the para of the pyridinium group;
  styrylazolium having formula and the geometric isomers thereof:

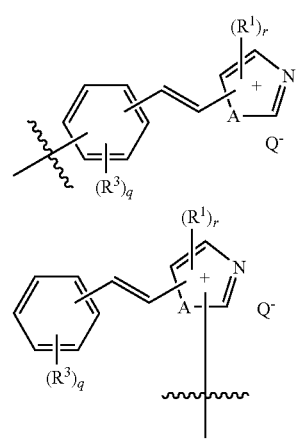

where:
  A represents a sulfur atom, an oxygen atom, or an $NR^2$ or $C(R^2)_2$ group; and

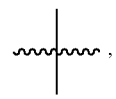, $Q^-$, r, q, $R^1$, $R^2$, and $R^3$ are as defined previously, preferably the

bond is found on the phenyl in the para position of the stryryl group,
  styrylpyrazine,
  chalcone,
  (thio)cinnamate and (thio)cinnamamide,
  maleimide,
  (thio)coumarin,
  thymine,
  uracil,
  butadiene
  anthracene,
  pyridone,
  pyrrolizinone,
  acridizinium salts, furanone,
phenylbenzoxazole, and
derivatives thereof.

According to a particular embodiment, the photo-dimerizable pendant group(s) i) of the invention are chosen from:
a) photo-dimerizable group(s) bearing a stilbazolium function having formula (Ia) or (Ib):

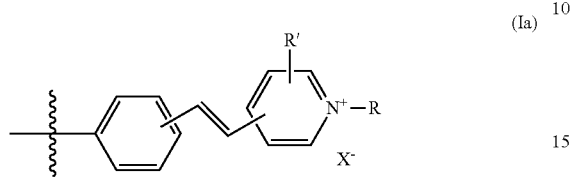
(Ia)

Formula (Ia) in which:
R represents a hydrogen atom, or a $C_1$-$C_4$ alkyl or $C_1$-$C_4$ hydroxyalkyl group,
R' represents a hydrogen atom or a $C_1$-$C_4$ alkyl group, and
X⁻ denotes an anionic counterion especially chosen from halide ions such as chlorides, bromides, iodides, perchlorates, tetrafluoroborates, methyl sulfate, phosphates, sulfates, methanesulfonates, p-toluenesulfonate; preferably the styryl group is found in the para of the pyridinium group and/or para to the

bond;

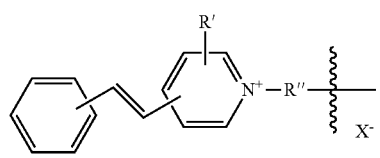
(Ib)

Formula (Ib) in which
R" denotes a divalent alkylene substituent having from 2 to 8 carbon atoms,
R' represents a hydrogen atom or a $C_1$-$C_4$ alkyl group, and
X⁻ has the same meaning as that described for the preceding formula (Ia);
where

has the same meaning as previously;
preferably the styryl group is found in the para of the pyridinium group;

or
b) photo-dimerizable groups bearing a styrylazolium function having formula (IIa):

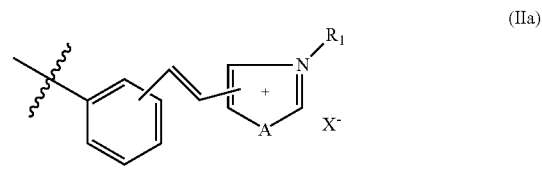
(IIa)

in which:
$R_1$ denotes a hydrogen atom or a $C_1$-$C_4$ alkyl or $C_1$-$C_4$ hydroxyalkyl group;
A denotes a sulfur atom, an oxygen atom or an NR' or $C(R')_2$ group, R'; where R' represents a hydrogen atom or a $C_1$-$C_4$ alkyl group, and R' preferably represents a hydrogen atom; and
X⁻ has the same meaning as that described for the preceding formula (Ia);
where

has the same meaning as previously;
preferably the styryl group is found on the para of the phenyl group

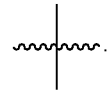

Such chemical groups bear activated double bonds, and as such the photo-dimerization of these double bonds starts spontaneously in the UVA range, without requiring a photoinitiator.

According to one particular embodiment, the composition of the invention is free of photoinitiators.

According to the present invention the polymer includes ii) one or more pendant hydrophobic groups.

As pendant hydrophobic group, mention may be made of:
saturated or unsaturated ($C_1$-$C_{30}$)alkyl groups optionally substituted and/or interrupted by one or more heteroatoms,
alkenyl groups,
aryl groups such as phenyl, pyridyl, furyl, indoyl, benzofuryl, thiophenyl, imizadoyl, oxazoyl, thiazoyl, pyrazinyl, pyrimidinyl;
fluorinated groups such as fluorocarbon groups such as —$CF_3$, —$CHF_2$, —$OCF_3$, —$SCF_3$, $CF_3C(O)$—,
silicone groups such as —$SiR_aR_bR_c$ such as —Si$(CH_3)_3$, polydimethylsiloxane-PDMS, —Si$(OR)_3$, PDMS α, ω diaminopropyl, PDMS α, ω dihydroxyalkyl, PDMS α, ω dicarboxyalkyl, where $R_a$, $R_b$ and $R_c$, identical or different, represent a ($C_1$-$C_8$)alkyl group optionally interrupted and/or terminated by one or more non-contiguous heteroatoms such as O or S; and R represents a ($C_1$-$C_6$)alkyl group.

Preferably the pendant hydrophobic group(s) are chosen from a ($C_2$-$C_{22}$)alkyl group, more preferentially a ($C_3$-$C_{16}$) alkyl group. More preferably ($C_8$-$C_{22}$)alkyl group, more preferentially a ($C_{10}$-$C_{16}$)alkyl group.

The polymer backbone may have varied nature. This polymer backbone may be natural or synthetic. As natural polymer backbones, mention may be made of polysaccharides.

As polysaccharides, mention may be made of xanthan, carrageenan, chitosan, cellulose and its derivatives, alginate, starch, dextran, pullulan, galactomannan and the biologically acceptable salts thereof, and derivatives thereof. As synthetic backbones, mention may be made of poly(vinyl) polymers and polydiorganosiloxanes.

Among poly(vinyl) polymers, mention may be made of partially or totally hydrolyzed polyvinylacetate, and of polyvinyl alcohol (PVA).

As regards the compounds containing photo-dimerizable groups bearing a stilbazolium function, they are obtained by reacting the polymer under consideration with a chemical entity including a group having formula (Ia) or (Ib).

Preferably, the chemical species including a group (Ia) bears a reactive group W of aldehyde or acetal type.

As chemical entities that can be used to graft styrylpyridinium groups, mention may especially be made of quaternary salts of 2-(4-formylstyryl)-pyridinium, 4-(4-formylstyryl)-pyridinium, 2-(3-formylstyryl)-pyridinium, N-methyl-2-(4-formylstyryl)pyridinium, N-methyl-3-(4-formylstyryl)-pyridinium, N-methyl-2-(3-formylstyryl)-pyridinium, N-methyl-2-(2-formylstyryl)pyridinium, N-ethyl-2-(4-formyl-styryl)-pyridinium, N-(2-hydroxy-ethyl)-2-(4-formylstyryl)-pyridinium, N-(2-hydroxyethyl)-4-(4-formylstyryl)-pyridinium, N-methyl-4-(4-formyl-styryl)-pyridinium, N-methyl-4-(3-formylstyryl)-pyridinium.

The anionic counterion of pyridinium quaternary moiety is especially selected from chloride, bromide, iodide, perchlorate, tetrafluoroborate, methosulfate, phosphate, sulfate, methanesulfonate or p-toluenesulfonate salts. Such chemical entities are described in GB-A-2030575.

Examples of species that may be mentioned include 4-(4-formylphenylethenyl)-1-methylpyridinium methosulfate, 1-(3-ethoxycarbonylmethyl)-4-[2-(4-formylphenyl) ethenyl]pyridinium bromide and 1-(methoxycarbonylpropyl)-4-[2-(4-formylphenyl)ethenyl]pyridinium bromide. Such species are described in US 2007/0 112 094.

Use is preferably made of n-methyl-4-(4-formylstyryl) pyridinium methyl sulfate (RN=74401-04-0), sold especially by the company Wako.

These polymers functionalized by photo-dimerizable groups such as those comprising a styryl group and hydrophobic groups, can be synthesized, as described below, using the protocol of T. Uhlich et al. (*Reactive & Functional Polymers*, 28, 55-40 (1995)).

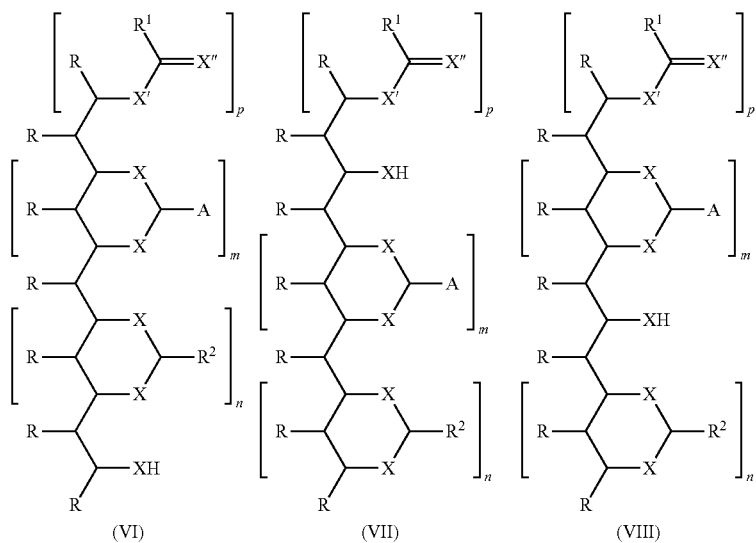

(VI) (VII) (VIII)

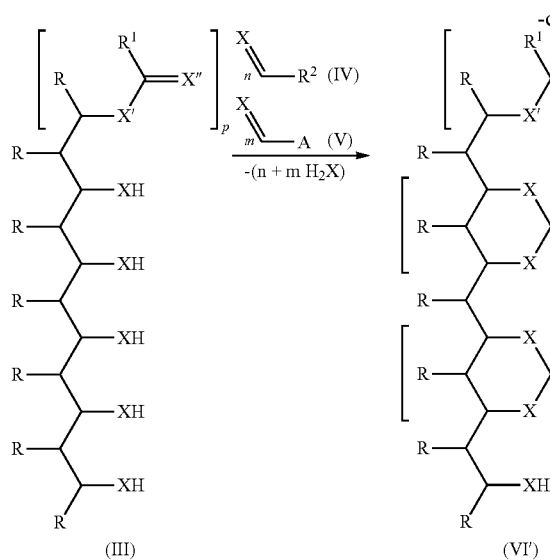
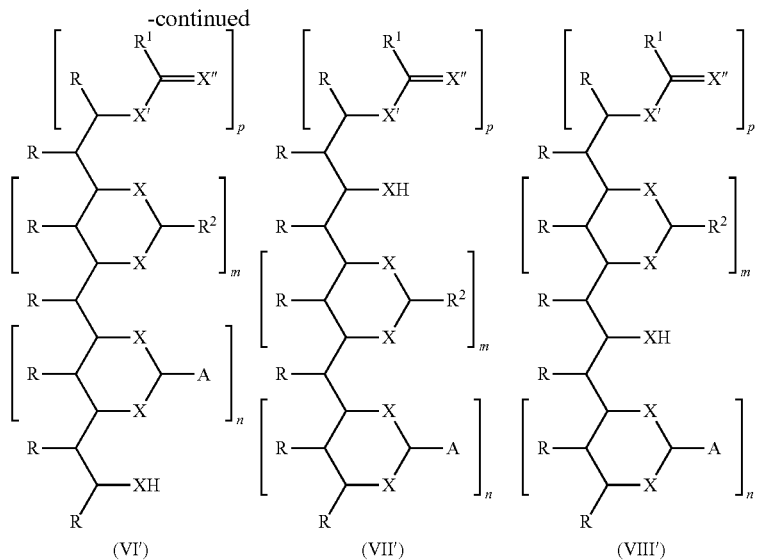

Compound having formula (III) to (VIII') in which,

R, identical or different, represents a hydrogen atom, or a $(C_1-C_{10})$alkyl group, optionally substituted and/or interrupted by one or more heteroatoms, preferably R represents a hydrogen atom or a $(C_1-C_4)$alkyl group such as methyl, ethyl, or propyl, more preferentially R represents a hydrogen atom;

$R^1$ represents a hydrogen atom, or a $(C_1-C_{10})$alkyl group, optionally substituted and/or interrupted by one or more heteroatoms, preferably $R^1$ represents a hydrogen atom or a $(C_1-C_4)$alkyl group;

$R^2$ represents a saturated or unsaturated $(C_1-C_{30})$alkyl group, optionally substituted and/or interrupted by one or more heteroatoms, an alkenyl group, an aryl group such as phenyl, pyridyl, furyl, indoyl, benzofuryl, thiophenyl, imizadoyl, oxazoyl, thiazoyl, pyrazinyl, pyrimidinyl; a fluorinated group such as a fluorocarbon group such as $—CF_3$, $—CHF_2$, $—OCF_3$, $—SCF_3$, $CF_3C(O)—$, a silicone group such as $—SiR_aR_bR_c$ such as $—Si(CH_3)_3$, polydimethylsiloxane-PDMS, $—Si(OR)_3$, PDMS α, ω diaminopropyl, PDMS α, ω dihydroxyalkyl, PDMS α, ω dicarboxyalkyl, with $R_a$, $R_b$ and $R_c$, identical or different, representing a $(C_1-C_8)$alkyl group optionally interrupted and/or terminated by one or more non-contiguous heteroatoms such as O, or S; and where R represents a $(C_1-C_6)$alkyl group; preferably $R^2$ represents a $(C_2-C_{22})$alkyl group, more preferentially $(C_3-C_{16})$alkyl; more preferably $(C_8-C_{22})$alkyl group, more preferentially a $(C_{10}-C_{16})$alkyl group;

A represents a group from a photo-dimerizable compound preferably styrylpyridinium such as (I), (II), $(A_1)$, $(A_2)$, (Ia), (Ib) or (IIa) as defined previously, more particularly chosen from $(A_1)$ or (Ia) as defined previously;

X represents an oxygen or sulfur, preferably oxygen, atom;

X', and X" represent an oxygen or sulfur atom or an $N(R^3)$ group with $R^3$ denoting a hydrogen atom or a $(C_1-C_4)$alkyl group; preferably, X' and X" represent an oxygen atom;

Mainly the products obtained have formula (VI).

Advantageously, these chemical entities react with a polyvinyl alcohol or polyvinyl acetal type polymer as described in the documents cited previously and also such as polymer (III) described in the scheme above for which X, X' and X" represent an oxygen atom, R and $R^1$ being as described previously.

For example, a grafted polyvinyl alcohol polymer including the following structure units results, where A represents a group (I), $(A_1)$ or (Ia):

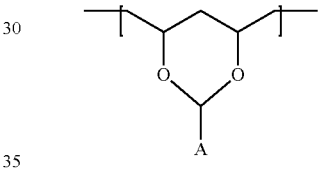

Polyvinyl alcohol polymers grafted with a styrylpyridinium group are especially described in the publication Ichimura K. et al., *Preparation and characteristics of photo-crosslinkable poly(vinyl alcohol)*, Journal of Polymer Science, Polymer Chemistry Edition, Vol. 20, 1419-1432 (1982).

The polymers may be obtained by reacting polyvinyl alcohol or partially hydrolyzed polyvinyl acetate with styrylpyridinium salts bearing a formyl or acetal group as described in GB-A-2 030 575, WO 96/29312, U.S. Pat. No. 5,061,603, GB-A-2 076 826 and EP-A-092 901.

Cellulose polymers grafted with styrylpyridinium groups are especially described in US 2007/0 112 094.

Preferably, the chemical entity including a group $(A_1)$ or (Ia) bears one reactive group that is a halogen atom such as chlorine.

In this variant, the chemical entity meets for example the formula:

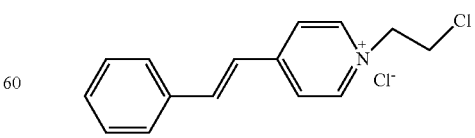

Advantageously, the photo-crosslinkable compound comprising groups (Ib) is for example obtained by reacting the entity above with the polysaccharide chosen from those defined previously.

As regards the compounds containing photo-dimerizable groups bearing a styrylazolium function, they are obtained by reacting the polymer with a chemical entity comprising a group having formula (IIa).

Preferably, the chemical entity including a group (IIa) bears a reactive group W of aldehyde or acetal type.

As chemical species that may be used to graft groups of styrylazolium type, mention may be made of those described in EP-A-313 220.

Advantageously, these chemical entities react with a polymer of polyvinyl alcohol or polyvinyl acetate type as described in the documents cited previously.

A grafted polyvinyl alcohol polymer including the following structure units results with B corresponding to the group

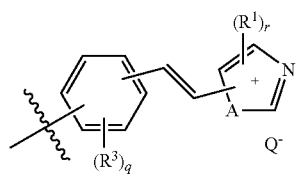

or (IIa) as defined previously:

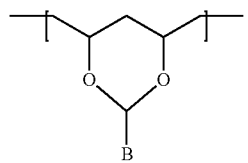

Polyvinyl alcohol polymers grafted with styrylazolium groups are described especially in EP-A-313 220. In said document, these polymers may be obtained by reaction of polyvinyl alcohol or partially hydrolyzed polyvinyl acetate with styrylazolium salts bearing an aldehyde or acetal group.

According to one embodiment, the polymer bearing (a) photo-dimerizable group(s) and (b) hydrophobic group(s) is in the form of particles, in particular of dispersed particles. Thus, in this latter case, the polymer particles are very preferentially polyvinyl alcohol particles.

According to a preferred embodiment, the polymer bearing (a) photo-dimerizable group(s) and (b) hydrophobic group(s) of the invention is soluble in the cosmetic medium.

Thus, according to one embodiment variant, the polymer is a polyvinyl alcohol (PVA) polymer partly functionalized with one or more hydroxyl functions and one or more functions having formula (IX):

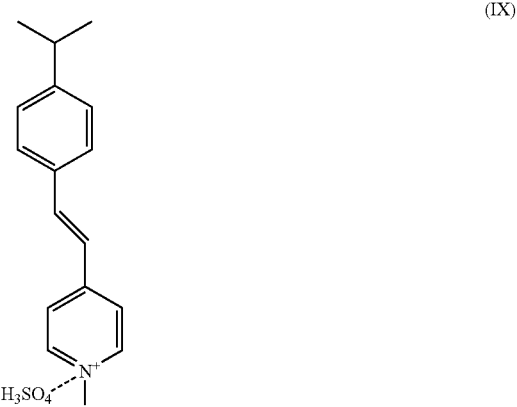

The degree of polymerization of PVA may be between 100 and 5000 and the level of substitution, in % of functions having formula (I) as defined above, may be between 0.1 and 25.

The following scheme represents one variant where the polymer is the polymer (III) as defined previously bearing functions grafted by stylbazolium entities such as those having formula (A1) as defined previously, which can cross-link under the effect of light, as illustrated below.

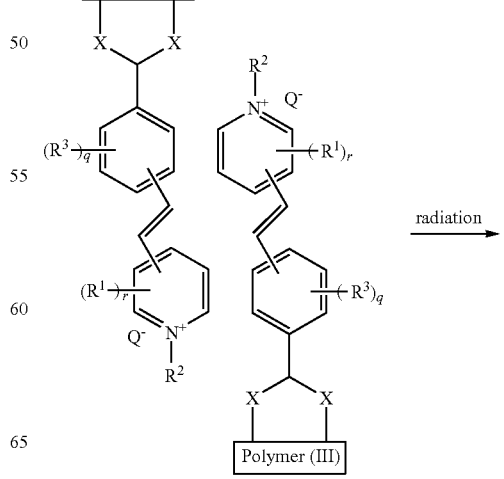

-continued

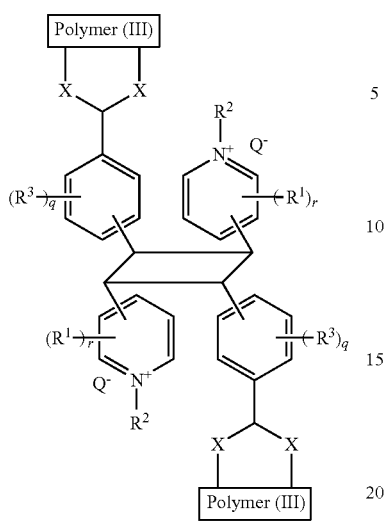

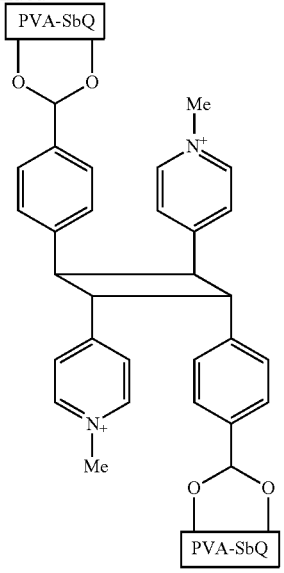

These materials react to radiation that may include both a UV visible light component, particularly a low dose of UV.

Preferentially, the following scheme represents the polymer which is PVA-SbQ (polymer of polyvinyl acetate type bearing a few hydrolyzed functions and a few functions grafted with stilbazolium entities), which can crosslink under the effect of light, as illustrated below.

These materials are particularly appreciated since they do not require a photoinitiator and react with radiation that may include both UV light and visible light, in particular a low dose of UV.

Pendants groups being reactive in both UV light and visible light are preferred.

According to another embodiment variant, the photo-crosslinkable compound is featured by a natural polymer that is functionalized with photo-dimerizable groups and hydrophobic groups.

It may especially be a polysaccharide that may especially be chosen from chondroitin sulfate, keratan, keratan sulfate, heparin, heparin sulfate, xanthan, carrageenan, hyaluronic acid, chitosan, cellulose and derivatives thereof, alginate, starch, dextran, pullulan, galactomannan and biologically acceptable salts thereof.

The degree of functionalization is of course adjusted be able to provide the degree of crosslinking required during activation.

According to the invention, the degree of functionalization with photo-dimerizable units is at least 0.1%, or even at least 0.5%, or even at least 2%.

Preferably, in a composition according to the invention, the photo-dimerizable groups are borne by a polyvinylacetate or polysaccharide polymer.

The crosslinkable polymer may be carried in an aqueous medium.

The composition may contain a single polymer bearing photo-dimerizable pendant groups that may or may not be of different nature.

Use may also be made of a mixture of polymers having different functions.

Consequently, the reactions may take place between two photo-dimerizable groups that may or may not be of the same chemical nature.

The activated double bonds may react with another double bond of the same chemical nature or may react with another double bond of different chemical nature.

As examples of polymers useful in the invention, mention may be made of the polymer PVA comprising the pendant groups below called PVA-SbQ-propional in which the quantity of SbQ units is inclusively between 0.5 and 5 mol %, preferably between 2 and 4 mol %, for example of the order of 2 mol %, the quantity of propional groups is inclusively between 2 and 20 mol %, preferably between 5 and 15 mol %, for example of the order of 10 mol %, the quantity of hydroxyl groups is inclusively between 50 and 97.5 mol %, preferably between 60 and 97.5 mol %, for example about 86 mol %:

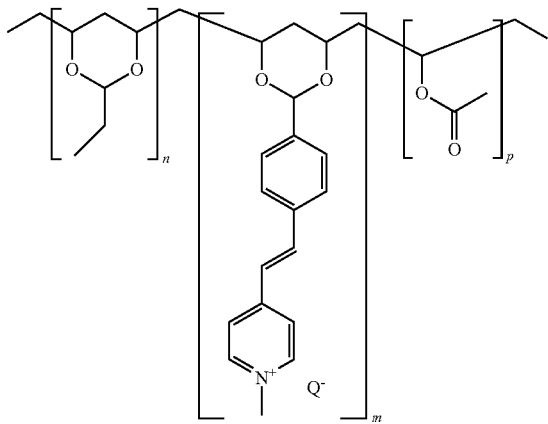

with Q⁻ as defined previously preferably mesylate $CH_3OSO_3^-$;

According to one particular embodiment, the molecular weight Mw of the PVA is between 10000 and 100000 g/mol and preferably between 25000 and 80000 g/mol.

According to one particular embodiment, the molecular weight Mw is of the order of 27000 g/mol.

The polymer(s) including at least one photo-dimerizable group and one hydrophobic group preferably represent 0.01 to 25%, better 0.1 to 20%, and even better 1 to 15% of the total weight of the composition.

The composition according to the invention may also comprise an effective quantity of at least one photosensitizing agent.

In the sense of the present invention, photosensitizing agent is understood to mean an ingredient that modifies the irradiation wavelength, thereby triggering the photo-dimerization reaction.

For example, the photo-dimerization of dimethylmaleimide groups is triggered by irradiation centred on the wavelength range from 270 to 300 nm. In the presence of a photosensitizing agent such as thioxanthone, photo-dimerization becomes effective with irradiation centred on the wavelength domain ranging from 360 to 430 nm.

Among the photosensitizers that can be used according to the invention, mention may especially be made of thioxanthone, rose Bengal, phloxine, eosin, erythrosine, fluorescein, acriflavine, thionine, riboflavin, proflavine, chlorophylls, hematoporphyrin, methylene blue and mixtures thereof.

In practice, the photosensitizing agent that can be used according to the invention represents 0.00001% to 5% of the total weight of the composition.

The composition may also comprise one or more fatty substances.

"Fatty substance" means an organic compound that is insoluble in water at standard temperature (25° C.) and at atmospheric pressure (760 mmHg, i.e. 1.013×10⁵ Pa), i.e. with a solubility of less than 5%, preferably of less than 1% and even more preferentially of less than 0.1%.

Fatty substances are generally soluble in organic solvents under the same temperature and pressure conditions, for instance chloroform, ethanol, benzene, liquid petroleum jelly or decamethylcyclopentasiloxane.

The fatty substances may be solid or liquid, preferably liquid.

The liquid fatty substances that may be used in the invention are liquid at ambient temperature (25° C.) and under atmospheric pressure (760 mmHg, i.e. 1.013×10⁵ Pa). They preferably have a viscosity of less than or equal to 2 Pa·s, better still less than or equal to 1 Pa·s, and even better still less than or equal to 0.1 Pa·s at a temperature of 25° C. and at a shear rate of 1 s⁻¹.

The liquid fatty substances that may be used in the composition according to the invention are generally not oxyalkylenated and preferably do not contain any carboxylic acid COOH functions.

Preferably, the liquid fatty substances are chosen from hydrocarbons, fatty alcohols, fatty esters, fatty ethers and silicones, and mixtures thereof.

Even more preferentially, they are chosen from hydrocarbons, fatty alcohols, fatty esters and silicones, which are preferably volatile, and mixtures thereof.

"Liquid hydrocarbon" means a hydrocarbon composed solely of carbon and hydrogen atoms, which is liquid at standard temperature (25° C.) and at atmospheric pressure (760 mmHg, i.e. 1.013×10⁵ Pa), which is of mineral or plant or synthetic origin.

More particularly, the liquid hydrocarbons are chosen from:
- linear or branched, optionally cyclic, $C_6$-$C_{16}$ alkanes. Examples that may be mentioned include hexane, undecane, dodecane, tridecane, and isoparaffins, for instance isohexadecane, isododecane and isodecane, and mixtures thereof.
- linear or branched hydrocarbons of mineral, animal or synthetic origin with more than 16 carbon atoms, such as liquid paraffins, liquid petroleum jelly, polydecenes, hydrogenated polyisobutene such as the product sold under the brand name Parleam® by NOF Corporation, and squalane.

In a preferred variant, the liquid hydrocarbon(s) are chosen from linear or branched, optionally cyclic, $C_6$-$C_{16}$ alkanes.

The term "liquid fatty alcohol" means a non-glycerolated and non-oxyalkylenated fatty alcohol which is liquid at standard temperature (25° C.) and at atmospheric pressure (760 mmHg; i.e. 1.013×10⁵ Pa).

Preferably, the liquid fatty alcohols of the invention comprise from 8 to 30 carbon atoms and better still from 8 to 20 carbon atoms.

The liquid fatty alcohols of the invention may be saturated or unsaturated.

The saturated liquid fatty alcohols are preferably branched. They may optionally comprise in their structure at least one aromatic or non-aromatic ring. Preferably, they are acyclic.

More particularly, the saturated liquid fatty alcohols of the invention are chosen from octyldodecanol, isostearyl alcohol and 2-hexyldecanol.

Octyldodecanol is most particularly preferred.

The unsaturated liquid fatty alcohols contain in their structure at least one double or triple bond, and preferably one or more double bonds. When several double bonds are present, there are preferably 2 or 3 of them, and they may be conjugated or unconjugated.

These unsaturated fatty alcohols may be linear or branched.

They may optionally comprise in their structure at least one aromatic or non-aromatic ring. Preferably, they are acyclic.

More particularly, the unsaturated liquid fatty alcohols of the invention are chosen from oleyl alcohol, linoleyl alcohol, linolenyl alcohol and undecylenyl alcohol.

Oleyl alcohol is most particularly preferred.

"Liquid fatty ester" means an ester derived from a fatty acid and/or from a fatty alcohol, that is liquid at standard temperature (25° C.) and at atmospheric pressure (760 mmHg, i.e. $1.013 \times 10^5$ Pa).

The esters are preferably liquid esters of saturated or unsaturated, linear or branched, $C_1$-$C_{26}$ aliphatic monoacids or polyacids and of saturated or unsaturated, linear or branched, $C_1$-$C_{26}$ aliphatic monoalcohols or polyalcohols, the total number of carbon atoms in the esters being greater than or equal to 10.

For the esters of monoalcohols, preferably at least one from among the alcohol and the acid from which the esters of the invention are obtained is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of mono-, di- or tricarboxylic acids and of $C_4$-$C_{26}$ non-sugar di-, tri-, tetra- or pentahydroxylated alcohols may also be used.

Mention may be made especially of diethyl sebacate, diisopropyl sebacate, bis(2-ethylhexyl) sebacate, diisopropyl adipate, di-n-propyl adipate, dioctyl adipate, bis(2-ethylhexyl) adipate, diisostearyl adipate, bis(2-ethylhexyl) maleate, triisopropyl citrate, triisocetyl citrate, triisostearyl citrate, glyceryl trilactate, glyceryl trioctanoate, trioctyldodecyl citrate, trioleyl citrate, neopentyl glycol diheptanoate, and diethylene glycol diisononanoate.

The composition may further comprise, as liquid fatty ester, sugar esters and diesters of $C_6$-$C_{30}$ fatty acids, preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include saccharose, glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be selected especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or unconjugated carbon-carbon double bonds.

The esters according to this variant may also be chosen from mono-, di-, tri- and tetraesters, and polyesters, and mixtures thereof.

These esters may be, for example, oleates, laurates, palmitates, myristates, behenates, cocoates, stearates, linoleates, linolenates, caprates and arachidonates, and mixtures thereof, such as, especially, oleopalmitate, oleostearate or palmitostearate mixed esters.

More particularly, use is made of monoesters and diesters and especially of sucrose, glucose or methylglucose mono- or dioleates, stearates, behenates, oleopalmitates, linoleates, linolenates or oleostearates.

An example that may be mentioned is the product sold under the name Glucate® DO by Amerchol, which is a methylglucose dioleate.

Finally, use may also be made of natural or synthetic glycerol esters of mono-, di- or triacids.

Among these, mention may be made of plant oils.

As oils of plant origin or synthetic triglycerides that may be used in the composition of the invention as liquid fatty esters, examples that may be mentioned include:

triglyceride oils of plant or synthetic origin, such as liquid fatty acid triglycerides containing from 6 to 30 carbon atoms, for instance heptanoic or octanoic acid triglycerides, or alternatively, for example, sunflower oil, maize oil, soya bean oil, marrow oil, grapeseed oil, sesame oil, hazelnut oil, apricot oil, macadamia oil, arara oil, castor oil, avocado oil, olive oil, rapeseed oil, coconut oil, wheatgerm oil, sweet almond oil, safflower oil, candlenut oil, camelina oil, tamanu oil, babassu oil and pracaxi oil, caprylic/capric acid triglycerides, for instance those sold by Stéarineries Dubois or those sold under the names Miglyol® 810, 812 and 818 by Dynamit Nobel, jojoba oil and shea butter oil.

Liquid fatty esters derived from monoalcohols will preferably be used as esters according to the invention.

Isopropyl myristate or isopropyl palmitate are particularly preferred.

The liquid fatty ethers are chosen from liquid dialkyl ethers such as dicaprylyl ether.

The liquid fatty substance(s) that may be used in the composition according to the invention may be chosen from silicones.

Preferably, the liquid silicone(s) are chosen from polydialkylsiloxanes, especially polydimethylsiloxanes (PDMS), and organomodified polysiloxanes including at least one functional group chosen from amino groups, aryl groups and alkoxy groups.

Organopolysiloxanes are defined in greater detail in Walter Noll's *Chemistry and Technology of Silicones* (1968), Academic Press. They may be volatile or non-volatile.

The liquid non-volatile silicones that may be used in the composition according to the invention may preferably be liquid non-volatile polydialkylsiloxanes, polyorganosiloxanes modified with organic functional groups chosen from amine groups, aryl groups and alkoxy groups, and also mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a non-limiting manner, of the following commercial products:

the Silbione® oils of the 47 and 70 047 series or the Mirasil® oils sold by Rhodia;

the oils of the Mirasil® series sold by Rhodia;

the oils of the 200 series from Dow Corning;

the Viscasil® oils from General Electric and certain oils of the SF series (SF 96, SF 18) from General Electric.

Mention may also be made of polydimethylsiloxanes having dimethylsilanol end groups known as dimethiconol (CTFA), such as the oils in the 48 series from Rhodia.

The organomodified silicones that may be used in accordance with the invention are silicones as defined above and comprising in their structure one or more organic functional groups attached via a hydrocarbon-based group.

The organomodified silicones may be polydiarylsiloxanes, especially polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:
- the Silbione® oils of the 70 641 series from Rhodia;
- oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN 1000 and PH1000;
- certain oils of the SF series from General Electric, such as SF 1023, SF 1154, SF 1250 and SF 1265.

Among the organomodified silicones, mention may also be made of polyorganosiloxanes comprising:
- substituted or unsubstituted amine groups, for instance the products sold under the names GP 4 Silicone Fluid and GP 7100 by Genesee. The substituted amine groups are in particular $C_1$-$C_4$ aminoalkyl groups;
- alkoxy groups such as the product sold under the name Silicone Copolymer F-755 by SWS Silicones, and Abil Wax® 2428, 2434 and 2440 by Goldschmidt.

The volatile silicones are more particularly chosen from those with a boiling point of between 60° C. and 260° C., and even more particularly from:

(i) cyclic silicones comprising from 3 to 7 and preferably 4 to 6 silicon atoms.

These are, for example, octamethylcyclotetrasiloxane sold especially under the name Volatile Silicone 7207 by Union Carbide or Silbione 70045 V 2 by Rhodia, decamethylcyclopentasiloxane sold under the name Volatile Silicone 7158 by Union Carbide, and Silbione 70045 V 5 by Rhodia, and mixtures thereof.

Mention may also be made of cyclocopolymers of the dimethylsiloxane/methylalkylsiloxane type, such as Volatile Silicone FZ 3109 sold by Union Carbide, of chemical structure:

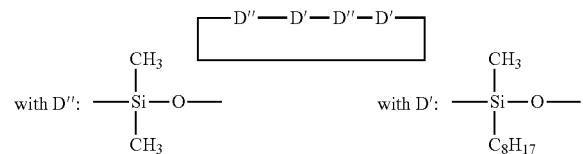

Mention may also be made of mixtures of cyclic silicones with organosilicon compounds, such as the mixture of octamethylcyclotetrasiloxane and tetrakis(trimethylsilyl) pentaerythritol (50/50) and the mixture of octamethylcyclotetrasiloxane and oxy-1,1'-bis(2,2,2',2',3,3'-hexatrimethylsilyloxy)neopentane;

Linear volatile silicones containing 2 to 9 silicon atoms and having a viscosity of less than or equal to $5 \times 10^{-6}$ m$^2$/s at 25° C. Examples include hexamethyldisiloxane, octamethyltrisiloxane and decamethyltetrasiloxane sold especially under the name SH 200 by Toray Silicone. Silicones belonging to this category are also described in the article published in Cosmetics and Toiletries, Vol. 91, January 76, pp. 27-32, Todd & Byers "Volatile Silicone Fluids for Cosmetics". Preferably, the linear volatile silicones contain from 2 to 7 silicon atoms and better still from 3 to 6 silicon atoms.

Preferably, the volatile silicones are chosen from cyclic silicones comprising from 4 to 6 silicon atoms and linear silicones containing 4 to 6 silicon atoms.

Preferably, the silicones are chosen from volatile silicones.

Preferably, the liquid fatty substance(s) are chosen from linear or branched $C_6$-$C_{16}$ alkanes, such as undecane, tridecane or isododecane, and mixtures thereof; triglyceride oils of plant origin such as copra oil or avocado oil; fatty esters such as isopropyl myristate; branched fatty alcohols; linear or cyclic volatile silicones, comprising fewer than 7 silicon atoms, preferably from 4 to 6 silicon atoms; and mixtures thereof.

Even more preferentially, the liquid fatty substances are chosen from linear or branched $C_6$-$C_{16}$ alkanes, in particular such as isododecane, undecane or tridecane, and mixtures thereof, and linear or cyclic volatile silicones, comprising less than 7 silicon atoms, preferably from 4 to 6 silicon atoms.

"Non-liquid fatty substance" means a solid compound or a compound that has a viscosity of greater than 2 Pa·s at a temperature of 25° C. and at a shear rate of 1 s$^{-1}$.

In a first variant of the invention, the non-liquid fatty substances are chosen from non-liquid fatty substances that do not contain silicon. Preferably, the non-liquid fatty substances that do not contain silicon are chosen from fatty alcohols, fatty acid and/or fatty alcohol esters, non-silicone waxes, fatty amines and fatty ethers, which are non-liquid and preferably solid.

More particularly, the non-liquid fatty alcohols according to the invention are chosen from linear or branched, saturated or unsaturated alcohols containing from 8 to 30 carbon atoms.

Examples that may preferably be mentioned include cetyl alcohol, stearyl alcohol and a mixture thereof (cetylstearyl alcohol). Cetylstearyl alcohol is more particularly used.

The non-liquid esters of fatty acids and/or of fatty alcohols that may be used in the composition according to the invention are generally chosen from solid esters derived from $C_9$-$C_{26}$ fatty acids and from $C_9$-$C_{26}$ fatty alcohols.

Examples that may preferably be mentioned include octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

The non-silicone wax(es) are chosen especially from carnauba wax, candelilla wax, esparto wax, paraffin wax, ozokerite, plant waxes, such as olive tree wax, rice wax, hydrogenated jojoba wax and absolute flower waxes, such as the blackcurrant blossom essential wax sold by Bertin (France), and animal waxes, such as beeswaxes or modified beeswaxes (cerabellina), and ceramides.

The solid amides that may be used in the composition according to the invention are chosen from ceramides and ceramide analogues, such as the natural or synthetic glycoceramides corresponding to formula (IV) below:

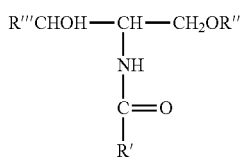 (IV)

in which:
- R' denotes a linear or branched, saturated or unsaturated alkyl substituent derived from $C_{14}$-$C_{30}$ fatty acids, this substituent possibly being substituted with a hydroxyl group in the alpha position, or a hydroxyl group in the omega position which is esterified with a saturated or unsaturated $C_{16}$-$C_{30}$ fatty acid;
- R" denotes a hydrogen atom or a (glycosyl)n, (galactosyl)m or sulfogalactosyl substituent, in which n is an integer ranging from 1 to 4 and m is an integer ranging from 1 to 8;
- R'" denotes a $C_{15}$-$C_{26}$ hydrocarbon-based substituent, saturated or unsaturated in the alpha position, where this substituent may be substituted with one or more $C_1$-$C_{14}$ alkyl substituents;

With the proviso that, in the case of natural ceramides or glycoceramides, R'" may also denote a $C_{15}$-$C_{26}$ alpha-hydroxyalkyl substituent, the hydroxyl group being optionally esterified with a $C_{16}$-$C_{30}$ alpha-hydroxy acid.

The ceramides that are preferred in the context of the present invention are those described by Downing in Arch. Dermatol, Vol. 123, 1381-1384, 1987, or those described in French patent FR 2 673 179.

The ceramide(s) more particularly preferred that may be used in the composition according to the invention are the compounds for which R' denotes a saturated or unsaturated alkyl derived from $C_{16}$-$C_{22}$ fatty acids; R" denotes a hydrogen atom; and R'" denotes a linear, saturated $C_{15}$ substituent.

Preferentially, the following compounds may especially be chosen: N-linoleoyldihydrosphingosine, N-oleoyldihydrosphingosine, N-palmitoyldihydrosphingosine, N-stearoyldihydrosphingosine, N-behenoyldihydrosphingosine, and a mixture of these compounds.

Even more preferentially, ceramides are used for which R' denotes a saturated or unsaturated alkyl substituent derived from fatty acids, R" denotes a galactosyl or sulfogalactosyl substituent and R'" denotes a —CH=CH—(CH$_2$)$_{12}$—CH$_3$ group.

Other waxes or waxy starting materials that may be used according to the invention are especially marine waxes such as those sold by Sophim under the reference M82, and waxes of polyethylene or of polyolefins in general.

The non-liquid fatty ethers that may be used in the composition according to the invention are chosen from dialkyl ethers and especially dicetyl ether and distearyl ether, alone or as a mixture.

In a second variant of the invention, the non-liquid fatty substance(s) may be chosen from silicone non-liquid fatty substances, such as silicone gums or resins.

The silicone gums that may be used in accordance with the invention are especially polydialkylsiloxanes and preferably polydimethylsiloxanes with high number-average molecular weights ranging from 200 000 to 1 000 000, used alone or as a mixture in a solvent.

Said solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:
- mixtures formed from a hydroxy-terminated polydimethylsiloxane chain or dimethiconol (CTFA), and from a cyclic polydimethylsiloxane, also known as cyclomethicone (CTFA), such as the product Q2 1401 sold by Dow Corning;
- mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;
- mixtures of two PDMS with different viscosities, and more particularly of a PDMS gum and of a PDMS oil, such as the product SF 1236 from General Electric. The product SF 1236 is a mixture of a gum SE 30 defined above with a viscosity of 20 m$^2$/s and of an oil SF 96 with a viscosity of 5×10$^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

(R7)2SiO2/2, (R7)3SiO1/2, R7SiO3/2 and SiO4/2 in which R7 denotes an alkyl having from 1 to 16 carbon atoms. Among these products, the ones that are particularly preferred are those in which R7 denotes a $C_1$-$C_4$ lower alkyl substituent, more particularly methyl.

Among these resins, mention may be made of the product sold under the name Dow Corning 593 or those sold under the names Silicone Fluid SS 4230 and SS 4267 by General Electric, which are silicones of dimethyl/trimethylsiloxane structure.

Mention may also be made of the trimethyl siloxysilicate-type resins sold especially under the names X22-4914, X21-5034 and X21-5037 by Shin-Etsu.

When they are present, the preferably liquid fatty substances are present in the composition in an amount ranging from 1 to 30%, better from 3 to 20% by weight and better still from 5 to 15% by weight, relative to the total weight of the composition.

The composition may also comprise one or more surfactants. As surfactants, mention may be made of anionic, amphoteric, zwitterionic, cationic or nonionic surfactants.

"Anionic surfactant" means a surfactant comprising, as ionic or ionizable groups, only anionic groups. These anionic groups are preferably chosen from the following groups:

—C(O)—OH, —C(O)—O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$—, =P(O)O$^-$—, =POH, =PO$^-$; the anionic parts comprising a cationic counterion such as those of an alkali metal, an alkaline-earth metal or an ammonium.

Mention may be made, as examples of anionic surfactants that can be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates, salts of alkyl monoesters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids; and the corresponding non-salified forms of all these compounds, the alkyl and acyl groups of all these compounds comprising from 6 to 40 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Mention may especially be made, as examples of amino alcohol salts, of mono-, di- and triethanolamine salts, mono-, di- or triisopropanolamine salts, 2-amino-2-methyl-1-propanol salts, 2-amino-2-methyl-1,3-propanediol salts and tris (hydroxymethyl)aminomethane salts.

Use is preferably made of alkali metal or alkaline-earth metal salts and in particular of sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, especially in the form of alkali metal, ammonium, amino alcohol and alkaline-earth metal salts, or a mixture of these compounds.

It is especially preferred to use ($C_{12}$-$C_{20}$)alkyl sulfates, ($C_{12}$-$C_{20}$)alkyl ether sulfates comprising from 2 to 20 ethylene oxide units, especially in the form of alkali metal, ammonium, amino alcohol and alkaline-earth metal salts, or a mixture of these compounds. Better still, it is preferred to use sodium lauryl ether sulfate containing 2.2 mol of ethylene oxide.

The amphoteric or zwitterionic surfactants that may be used in the present invention preferably do not contain silicon. They may especially be optionally quaternized secondary or tertiary aliphatic amine derivatives, in which the aliphatic group is a linear or branched chain containing from 8 to 22 carbon atoms, the said amine derivatives containing at least one anionic group, for instance a carboxylate, sulfonate, sulfate, phosphate or phosphonate group. Mention may be made in particular of ($C_8$-$C_{20}$)alkyl betaines, sulfo-betaines, ($C_8$-$C_{20}$)alkylamido($C_3$-$C_8$)alkyl betaines and ($C_8$-$C_{20}$)alkylamido($C_6$-$C_8$)alkyl sulfobetaines.

Among the optionally quaternized secondary or tertiary aliphatic amine derivatives that may be used, as defined above, mention may also be made of the compounds of respective structures (A10) and (A20) below:

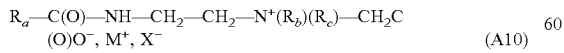

$$R_a\text{---}C(O)\text{---}NH\text{---}CH_2\text{---}CH_2\text{---}N^+(R_b)(R_c)\text{---}CH_2C(O)O^-, M^+, X^- \quad (A10)$$

Formula (A10) in which:
$R_a$ represents a $C_{10}$-$C_{30}$ alkyl or alkenyl group derived from an acid $R_a$COOH preferably present in hydrolyzed copra oil, or a heptyl, nonyl or undecyl group;
$R_b$ represents a β-hydroxyethyl group; and
$R_c$ represents a carboxymethyl group;

$M^+$ represents a cationic counterion derived from an alkali metal or alkaline-earth metal, such as sodium, an ammonium ion or an ion derived from an organic amine, and $X^-$ represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$)alkylaryl sulfonates, in particular methyl sulfate and ethyl sulfate; or alternatively $M^+$ and $X^-$ are absent;

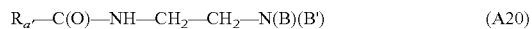

$$R_{a'}\text{---}C(O)\text{---}NH\text{---}CH_2\text{---}CH_2\text{---}N(B)(B') \quad (A20)$$

Formula (A20) in which:
B represents the group —$CH_2$—$CH_2$—O—X';
B' represents the group —$(CH_2)_z$Y', where z=1 or 2;
X' represents the group —$CH_2$—C(O)OH, —$CH_2$—C(O)OZ', —$CH_2$—$CH_2$—C(O)OH, —$CH_2$—$CH_2$—C(O)OZ', or a hydrogen atom;
Y' represents the group —C(O)OH, —C(O)OZ', —$CH_2$—CH(OH)—$SO_3$H or the group —$CH_2$—CH(OH)—$SO_3$—Z';
Z' represents a cationic counterion derived from an alkali metal or alkaline-earth metal, such as sodium, an ammonium ion or an ion derived from an organic amine;
$R_{a'}$ represents a $C_{10}$-$C_{30}$ alkyl or alkenyl group derived from an acid $R_a$—C(O)OH, which is preferably present in coconut oil or in hydrolyzed linseed oil, an alkyl group, especially a $C_{17}$ group and its iso form, or an unsaturated $O_{17}$ group.

These compounds having formula (A10) and (A20) are classified in the CTFA dictionary, 5th edition, 1993, under the names disodium cocoamphodiacetate, disodium lauroamphodiacetate, disodium caprylamphodiacetate, disodium caproamphodiacetate, disodium cocoamphodipropionate, disodium lauroamphodipropionate, disodium caprylamphodipropionate, disodium caproamphodipropionate, lauroamphodipropionic acid and cocoamphodipropionic acid.

By way of example, mention may be made of the cocoamphodiacetate sold by Rhodia under the trade name Miranol® C2M Concentrate.

Use may also be made of compounds having formula (A'20):

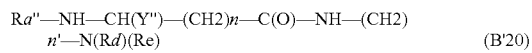

$$Ra''\text{---}NH\text{---}CH(Y'')\text{---}(CH2)n\text{---}C(O)\text{---}NH\text{---}(CH2)n'\text{---}N(Rd)(Re) \quad (B'20)$$

In which formula:
Y" represents the group —C(O)OH, —C(O)OZ", —CH2-CH(OH)—SO3H or the group —CH2-CH(OH)—SO3-Z";
Rd and Re, independently of each other, represent a $C_1$-$C_4$ alkyl or hydroxyalkyl substituent;
Z" represents a cationic counterion derived from an alkali metal or alkaline-earth metal, such as sodium, an ammonium ion or an ion derived from an organic amine;
Ra" represents a $C_{10}$-$C_{30}$ alkyl or alkenyl group derived from an acid Ra"'—C(O)OH, which is preferably present in coconut oil or in hydrolyzed linseed oil;
n and n', independently of each other, denote an integer ranging from 1 to 3.

Among the compounds having formula (A'20), mention may be made of the compound classified in the CTFA dictionary under the name sodium diethylaminopropyl cocoaspartamide and sold by Chimex under the name Chimexane HB.

Among the amphoteric or zwitterionic surfactants mentioned above, use is preferably made of ($C_8$-$C_{20}$)alkylbetaines such as cocoylbetaine, $(C_8-C_{20})$alkylamido$(C_3-C_8)$ alkylbetaines such as cocamidopropylbetaine, and mixtures thereof, and the compounds having formula (B'20) such as the sodium salt of diethylaminopropyl laurylaminosuccinamate (INCI name: sodium diethylaminopropyl cocoaspartamide) and mixtures thereof. More preferentially, the amphoteric or zwitterionic surfactant(s) are chosen from cocamidopropylbetaine and cocoylbetaine.

The cationic surfactant(s) that may be used in the composition according to the invention comprise, for example, optionally polyoxyalkylenated primary, secondary or tertiary fatty amine salts, quaternary ammonium salts, and mixtures thereof.

Examples of quaternary ammonium salts that may especially be mentioned include:

those corresponding to the general formula (A30) below:

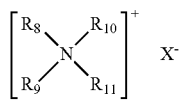

(A30)

Formula (A30) in which:

R8 to R11, which may be identical or different, represent a linear or branched aliphatic group comprising from 1 to 30 carbon atoms, or an aromatic group such as aryl or alkylaryl, it being understood that at least one of the groups R8 to R11 comprises from 8 to 30 carbon atoms and preferably from 12 to 24 carbon atoms; and $X^-$ represents an organic or inorganic anionic counterion, such as that chosen from halides, acetates, phosphates, nitrates, $(C_1-C_4)$alkyl sulfates, $(C_1-C_4)$alkyl- and $(C_1-C_4)$alkylarylsulfonates, in particular methyl sulfate and ethyl sulfate.

The aliphatic groups of R8 to R11 may also comprise heteroatoms especially such as oxygen, nitrogen, sulfur and halogens.

The aliphatic groups R8 to R11 are chosen, for example, from $C_1-C_{30}$ alkyl, $C_1-C_{30}$ alkoxy, polyoxy$(C_2-C_6)$alkylene, $C_1-C_{30}$ alkylamide, $(C_{12}-C_{22})$alkylamido$(C_2-C_6)$alkyl, $(C_{12}-C_{22})$alkyl acetate, and $C_1-C_{30}$ hydroxyalkyl groups, $X^-$ is an anionic counterion chosen from halides, phosphates, acetates, lactates, $(C_1-C_4)$alkyl sulfates, and $(C_1-C_4)$alkyl- or $(C_1-C_4)$alkylarylsulfonates.

Preference is given, among the quaternary ammonium salts having the formula (A3), firstly to tetraalkylammonium chlorides, such as, for example, dialkyldimethylammonium or alkyltrimethylammonium chlorides in which the alkyl group includes approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold as Ceraphyl® 70 by Van Dyk;

quaternary ammonium imidazoline salts, for instance those having formula (A40) below:

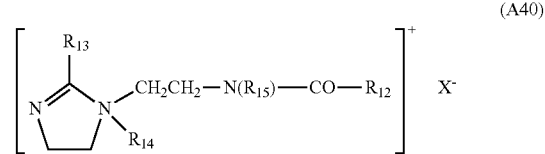

(A40)

Formula (A40) in which:

R12 represents an alkenyl or alkyl group comprising from 8 to 30 carbon atoms, for example tallow fatty acid derivatives;

R13 represents a hydrogen atom, a $C_1-C_4$ alkyl group or an alkenyl or alkyl group comprising from 8 to 30 carbon atoms;

R14 represents a $C_1-C_4$ alkyl group;

R15 represents a hydrogen atom or a $C_1-C_4$ alkyl group;

$X^-$ represents an organic or inorganic anionic counterion, such as that chosen from halides, phosphates, acetates, lactates, $(C_1-C_4)$alkyl sulfates, $(C_1-C_4)$alkyl or $(C_1-C_4)$ alkylaryl sulfonates.

R12 and R13 preferably denote a mixture of alkenyl or alkyl groups containing from 12 to 21 carbon atoms, for example tallow fatty acid derivatives, R14 denotes a methyl group, and R15 denotes a hydrogen atom. Such a product is sold, for example, under the name Rewoquat® W 75 by Rewo;

di- or triquaternary ammonium salts, in particular having formula (A5) below:

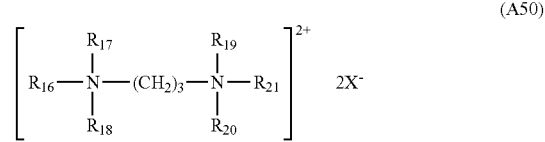

(A50)

Formula (A50) in which:

R16 denotes an alkyl group including approximately from 16 to 30 carbon atoms, which is optionally hydroxylated and/or interrupted with one or more oxygen atoms;

R17 is chosen from hydrogen, an alkyl group comprising from 1 to 4 carbon atoms and a group $—(CH_2)_3—N^+$(R16a)(R17a)(R18a), $X^-$;

R16a, R17a, R18a, R18, R19, R20 and R21, identical or different, are chosen from hydrogen and an alkyl group including from 1 to 4 carbon atoms; and $X^-$, identical or different, represent an organic or inorganic anionic counterion, such as that chosen from halides, acetates, phosphates, nitrates, alkyl$(C_1-C_4)$sulfates, alkyl$(C_1-C_4)$— or alkyl$(C_1-C_4)$aryl-sulfonates, in particular methylsulfate and ethylsulfate.

Such compounds are, for example, Finquat CT-P, sold by Finetex (Quaternium 89), and Finquat CT, sold by Finetex (Quaternium 75);

quaternary ammonium salts containing one or more ester functions, such as those having formula (A6) below:

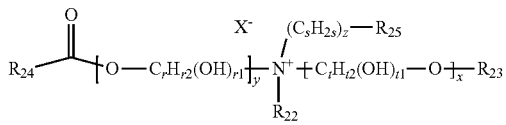

(A60)

Formula (A60) in which:
R22 is chosen from $C_1$-$C_6$ alkyl and $C_1$-$C_6$ hydroxyalkyl or dihydroxyalkyl groups;
R23 is chosen from:
  the group

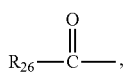

linear or branched, saturated or unsaturated $C_1$-$C_{22}$ hydrocarbon-based substituents R27,
  a hydrogen atom,
R25 is chosen from:
  the group

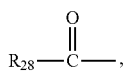

linear or branched, saturated or unsaturated $C_1$-$C_6$ hydrocarbon-based substituents R29,
  a hydrogen atom,
R24, R26 and R28, which may be identical or different, are chosen from linear or branched, saturated or unsaturated $C_7$-$C_{21}$ hydrocarbon-based substituents;
r, s and t, which may be identical or different, are integers ranging from 2 to 6,
r1 and t1, which may be identical or different, are equal to 0 or 1, with r2+r1=2r and t1+t2=2t,
y is an integer ranging from 1 to 10,
x and z, which may be identical or different, are integers ranging from 0 to 10;
$X^-$ represents an organic or inorganic anionic counterion, with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is an $R_{27}$ hydrocarbon group, it can be long and have from 12 to 22 carbon atoms or be short and have from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched saturated or unsaturated $C_{11}$-$C_{21}$ hydrocarbon groups, and more particularly from linear or branched or unsaturated $C_{11}$-$C_{21}$ alkyl and alkenyl groups.

Preferably, x and z, which may be identical or different, have the value 0 or 1.

Advantageously, y is equal to 1.

Preferably, r, s and t, which may be identical or different, have the value 2 or 3 and more particularly still are equal to 2.

The anionic counterion $X^-$ is preferably a halide, such as chloride, bromide or iodide; a ($C_1$-$C_4$)alkyl sulfate or a ($C_1$-$C_4$)alkyl- or ($C_1$-$C_4$)alkylarylsulfonate. However, use may be made of methanesulfonate, phosphate, nitrate, tosylate, an anion derived from an organic acid, such as acetate or lactate, or any other anion which is compatible with the ammonium having an ester function.

The anionic counterion $X^-$ is even more particularly chloride, methyl sulfate or ethyl sulfate.

Use is made more particularly in the composition according to the invention of the ammonium salts having formula (A60) in which:
  $R_{22}$ denotes a methyl or ethyl group,
  x and y are equal to 1,
  z is equal to 0 or 1,
  r, s and t are equal to 2,
  $R_{23}$ is chosen from:
    the

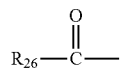

group
    methyl, ethyl or $C_{14}$-$C_{22}$ hydrocarbon-based groups,
    a hydrogen atom,
  $R_{25}$ is chosen from:
    the

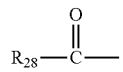

group
    a hydrogen atom,
  $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based substituents are linear.

Among the compounds having formula (A60), examples that may be mentioned include salts, especially diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium chloride or methyl sulfate, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by Henkel, Stepanquat® by Stepan, Noxamium® by CECA or Rewoquat® WE 18 by Rewo-Witco.

The composition according to the invention may contain, for example, a mixture of quaternary ammonium monoester, diester and triester salts with a weight majority of diester salts.

It is also possible to use the ammonium salts containing at least one ester function that are described in patents U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethyl-hydroxyethyl-methylammonium salts, and mixtures thereof, and more particularly behenyltrimethylammonium chloride, cetyltrimethylammonium chloride, and dipalmitoylethylhydroxyethylammonium methosulfate, and mixtures thereof.

Examples of nonionic surfactants that may be used in the composition used according to the invention are described, for example, in the "Handbook of Surfactants" by M. R. Porter, published by Blackie & Son (Glasgow and London), 1991, pp. 116-178. They are especially chosen from alcohols, α-diols and $(C_1-C_{20})$alkylphenols, these compounds being polyethoxylated, polypropoxylated and/or polyglycerolated, and containing at least one fatty chain comprising, for example, from 8 to 40 carbon atoms, it being possible for the number of ethylene oxide and/or propylene oxide groups to especially range from 1 to 200, and for the number of glycerol groups to especially range from 1 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, derivatives of N-alkyl glucamine and of N-acyl methylglucamine, aldobionamides, oxyethylenated and/or oxypropylenated silicones and amine oxides and mixtures thereof.

The composition according to the invention may also comprise an additional surfactant chosen from fatty acid esters of polyols.

According to the invention, "fatty acid esters of polyols" means esters of a fatty acid (or fatty acid polymers) and of a polyol in which the fatty acid comprises a $C_6-C_{22}$ and preferably $C_{16}-C_{20}$ alkyl chain and the polyol is chosen from glycerol, a polyglycerol and sorbitan, and mixtures thereof. The fatty acid may also be in a polymeric form, as is the case for polyhydroxystearic acid (12-hydroxystearic acid polymer).

According to a particular embodiment, the fatty acid ester of a polyol is a $C_{16}-C_{20}$ fatty acid ester of glycerol and/or sorbitan, and mixtures thereof.

As examples of linear or branched $C_{16}-C_{20}$ fatty acids, mention may be made of stearic acid, isostearic acid, lauric acid, myristic acid, palmitic acid. An example of a $C_{16}-C_{20}$ fatty acid polymer that may be mentioned is poly(12-hydroxystearic acid).

Preferably stearic acid, isostearic acid, or poly(12-hydroxystearic acid) and mixtures thereof will be used.

Polyglycerols are understood to mean compounds having formula:

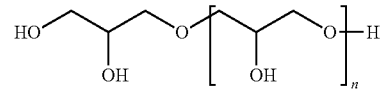

in which the degree of condensation n ranges from 1 to 11, preferably from 2 to 6 and even more preferentially from 3 to 6.

According to a specific embodiment, the ester of a fatty acid and a polyol contains 2 to 10 moles (units) of polyols, preferably 2 to 4 moles of polyols, in particular 2 to 4 units of glycerol or a mixture of polyglycerols (glycerol, di-, tri-, tetra-, penta-, oligoglycerols).

Even more preferentially, the ester of a fatty acid and a polyol contains 4 moles or units) of polyol, in particular 4 moles (or units) of glycerol.

According to one preferred embodiment, said ester of a fatty acid and a polyol is further a fatty acid ester, of a dicarboxylic acid having from 2 to 16 carbon atoms, preferably from 8 to 14 carbon atoms, such as azelaic acid, sebacic acid, dodecanedioic acid, and preferably sebacic acid $(C_{10})$, and a polyol.

As examples of esters of fatty acids and polyols that can be used in the composition of the invention, mention may be made of esters of isostearic acid and polyols and mixtures thereof, in particular the esters of isostearic acid and glycerol and/or of sorbitan, such as for example polyglycerolated (4 moles) isostearate (INCI name: Polyglyceryl-4 Isostearate) sold under the name Isolan GI34® by Goldschmidt, polyglycerolated (3 moles) diisostearate sold under the name Lameform TGI® by Cognis; polyglycerolated distearate (2 moles) sold under the name Emalex PGSA® by Nihon emulsion; polyglycerolated (10 moles) monoisostearate sold under the name Nikkol decaglyn 1-IS by Nihon Surfactant (INCI name: Polyglyceryl-10 isostearate); polyglyceryl-4 di isostearate polyhydroxystearate sebacate sold under the name Isolan GPS by Goldschmidt; the mixture of sorbitan isostearate and glycerol isostearate, such as the product sold under the name Arlacel 986 by ICI, the mixture of sorbitan isostearate and polyglycerol (3 moles) isostearate sold under the name Arlacel 1690 by Uniqema, the mixture of sorbitan isostearate and polyglycerol (3 moles) isostearate sold under the name Arlacel 1690® by Uniqema, PEG-30 dipolyhydrostearate sold under the name Arlacel P135 by Uniqema, and mixtures thereof.

The composition according to the invention may thereby comprise at least one surfactant chosen from fatty acid esters, preferably of $C_{16}-C_{20}$ fatty acids, in particular stearic acid or isostearic acid, and of a polyol chosen from glycerol and/or sorbitan.

The nonionic surfactants may also be chosen from mono- or polyoxyalkylenated or mono- or polyglycerolated nonionic surfactants. The oxyalkylene units are more particularly oxyethylene or oxypropylene units, or their combination, preferably oxyethylene units.

Mention may be made, as examples of oxyalkylenated nonionic surfactants, of:
  oxyalkylenated $(C_8-C_{24})$alkylphenols;
  saturated or unsaturated, linear or branched, oxyalkylenated $C_8-C_{30}$ alcohols;
  saturated or unsaturated, linear or branched, oxyalkylenated $C_8-C_{30}$ amides;

esters of saturated or unsaturated, linear or branched, $C_8$-$C_{30}$ acids and of polyethylene glycols;

polyoxyethylenated esters of saturated or unsaturated, linear or branched, $C_8$-$C_{30}$ acids and of sorbitol;

saturated or unsaturated oxyethylenated plant oils;

condensates of ethylene oxide and/or of propylene oxide, inter alia, alone or as mixtures;

oxyethylenated and/or oxypropylenated silicones;

and mixtures thereof.

The surfactants contain a number of moles of ethylene oxide and/or of propylene oxide of between 1 and 100, preferably between 2 and 50 and preferably between 2 and 30. Advantageously, the nonionic surfactants do not comprise any oxypropylene units.

In accordance with one preferred embodiment of the invention, the oxyalkylenated nonionic surfactants are chosen from oxyethylenated $C_8$-$C_{30}$ alcohols comprising from 1 to 100 mol of ethylene oxide; polyoxyethylenated esters of linear or branched, saturated or unsaturated $C_8$-$C_{30}$ acids and of sorbitol comprising from 1 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to formula (A70) below:

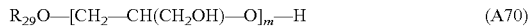

$$R_{29}O\text{---}[CH_2\text{---}CH(CH_2OH)\text{---}O]_m\text{---}H \quad (A70)$$

Formula (A70) in which:

$R_{29}$ represents a linear or branched $C_8$-$C_{40}$ and preferably $C_8$-$C_{30}$ alkyl or alkenyl substituent; and m represents a number ranging from 1 to 30 and preferably from 1 to 10.

As examples of compounds having formula (A70) that are suitable for use in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol and octadecanol comprising 6 mol of glycerol.

The alcohol having formula (A70) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

In accordance with another embodiment of the invention, the nonionic surfactants are chosen from polyoxyalkylenated silicones and more particularly polyoxyalkylenated polydimethylsiloxanes in which the polyoxyalkylene groups represent an alternated chain of oxygen atoms and linear or branched $C_2$ to $C_{10}$ alkylene groups, preferably $C_2$ to $C_6$ and more preferentially $C_2$ and/or $C_3$ (respectively ethylene and propylene), the number of alkylene groups being between 1 and 100, preferably between 5 and 50 and more preferentially between 10 and 40. As examples mention is made of PEG/PPG 18/18 dimethicone silicones sold under the name 5225C by Dow Corning.

Mention may also be made of mixed alkyl/polyoxyalkylene polydimethylsiloxanes in which the alkyl group is a linear or branched $C_8$ to $C_{30}$ chain, preferably $C_{12}$ to $C_{22}$, and the polyoxyalkylene group a chain alternating oxygen atoms and linear or branched $C_2$ to $C_{10}$ alkylene groups, preferably $C_2$ to $C_6$ and more preferentially $C_2$ and/or $C_3$ (respectively ethylene and propylene), the number of alkylene groups being between 1 and 100, preferably between 2 and 30 and more preferentially between 5 and 15, the distribution of the groups being such that the ethylene groups are the most numerous. As examples, mention is made of Cetyl PEG/PPG-10/1 dimethicone silicones such as proposed under the name ABIL EM 90 by Evonik.

Preferably, the surfactant used in the composition of the invention is a nonionic surfactant chosen from mono- or polyoxyalkylenated, particularly mono- or polyoxyethylenated, or mono- or polyoxypropylenated, nonionic surfactants, or a combination thereof, more particularly polyoxyalkylenated silicones.

When it comprises them, the composition comprises surfactants in amounts ranging from 0.1% to 50% by weight, better still from 0.5 to 30% by weight and even more preferentially from 0.5 to 20% by weight relative to the total weight of the composition.

The composition may comprise a cosmetically acceptable medium. The cosmetically acceptable medium that may be used in the compositions of the invention may comprise a solvent chosen from water, organic solvents, and a mixture thereof.

The organic solvents may be chosen from alcohols, polyols, polyol ethers and mixtures thereof, the alcohols being preferentially chosen from lower $C_1$-$C_6$ alkanols, and preferably chosen from ethanol, propanol and isopropanol, the polyols being preferentially chosen from propylene glycol, hexyleneglycol, glycerine, and pentanediol.

Preferably, the solvent(s) represent 0.1% to 99% of the total weight of the composition.

The composition is preferably aqueous.

According to this variant, the amount of water may range from 5 to 98% by weight, better from 15% by weight to 95% by weight, better still from 25 to 90% by weight and even more preferentially from 30 to 90% by weight, relative to the total weight of the composition. The composition according to the invention may also contain additives usually used in cosmetics, such as thickeners, preservatives, fragrances and colorants, and also most of the usual cosmetic agents.

These additives may be present in the composition according to the invention in an amount ranging from 0 to 20% by weight, relative to the total weight of the composition.

A person skilled in the art will take care to select these optional additives and amounts thereof so that they do not harm the properties of the compositions of the present invention.

The process of the invention comprises, after step a) of applying the composition, a step b) of irradiating the composition on the keratin substances to crosslink the polymer.

This irradiation may consist of illumination, with ambient light or with a source of artificial light, of the composition applied to the keratin substances.

The ambient or artificial light may emit radiation in the visible and/or UV range. Preferably, it emits at least a proportion of radiation in the UV range, for example a UV proportion of at least 2% of the total illuminating energy of the ambient light.

According to a particular embodiment, the exposure comprises, or even consists of, illumination with ambient light of the surface of said coat, in particular for a time of at least 1 minute.

The exposure time to the ambient light may range more particularly from 10 seconds to 30 minutes and especially from 2 to 15 minutes.

According to another particular embodiment, the exposure comprises, or even consists of, illumination with a source of artificial light of the surface of said coat.

The exposure time to said artificial light may range from 1 second to 20 minutes and in particular from 1 second to 1 minute.

The crosslinking may take place with natural or artificial light, for example using lighting with a lamp, a flash, a laser or LEDs, for example in the form of an LED array.

The artificial light source may emit radiation in the visible range and/or radiation in the UV range.

The light emitted may or may not be monochromatic. The wavelength of the emitted light is preferably centred on 365 nm, in particular between 100 nm and 500 nm and better still between 200 nm and 420 nm.

Advantageously, the crosslinking is initiated by simple illumination without the need for a photoinitiator.

Preferably, it will be a source of artificial light emitting energy between 0.5 and 5 W/cm$^2$, the exposure times being adapted in consequence.

The crosslinking may occur with reduced light intensity, the lighting system may produce this light intensity for example between 500 mJ/cm$^2$ and 10 J/cm$^2$.

The twofold characteristic of the absence of a photoinitiator and the relatively low light intensity is particularly advantageous since it makes it possible to limit the harmful effects of aggressive initiators or of prolonged exposure to intense light, in particular in the UV wavelengths.

A person skilled in the art will be capable of adapting the illumination characteristics, especially in terms of exposure time and of radiation wavelengths, with regard to the nature of the photo-crosslinkable compound(s) (A) used.

According to a preferred embodiment, the composition is applied to keratin fibres such as hair.

According to this embodiment, the composition may be applied to wet or dry, clean or non-clean keratin fibres. Preferably, the keratin fibres are dried after applying the composition and before irradiation.

In the process, before or after irradiation step b), a pause at room temperature, or high temperature, or under red light, may be included in the process.

According to another feature, the invention relates to a composition in the form of a water-in-oil emulsion comprising an aqueous phase dispersed in an oil phase, the composition comprising one or more surfactants and one or more photo-crosslinkable polymers including at least one photo-dimerizable pendant group and at least one hydrophobic pendant group.

The example below illustrates the invention without, however, limiting the scope thereof. The quantities are given, unless otherwise indicated, in percentages by weight.

EXAMPLES

Example 1

Polymer PVA-SbQ-Propional was obtained according to the process described previously.

4 g of PVA-SbQ propional solution at 5% Al of polymer was dried in a Teflon mould to form a PVA-SbQ propional film. The film obtained was irradiated under UVA at 365 nm for an energy of 8 J/cm$^2$. The film was then placed in a beaker of water with stirring for 48 h. The film obtained is insoluble and remains intact after 1 h. After 48 h, the film is a little fragmented, in quite large pieces.

4 g of PVA-SbQ solution at 5% Al of polymer was dried in a Teflon mould to form a PVA-SbQ film. The film obtained was irradiated under UVA at 365 nm for an energy of 8 J/cm$^2$. The film was then placed in a beaker of water with stirring for 48 h. The film fragments after 1 h. After 48 h, the film remains as insoluble but fragments in more pieces.

Example 2

The following compositions were made in inverse emulsion form (quantity in % weight of active ingredient)

|  | A (Invention 1) | B (Invention 2) | C (Comparative) | Control |
|---|---|---|---|---|
| Isopropyl myristate | 10 | 10 | 10 | 10 |
| Propylene glycol | 2.5 | 2.5 | 2.5 | 2.5 |
| Cetyl PEG/PPG-10/1 dimethicone | 1 | 1 | 1 | 1 |
| PVA-SbQ* |  |  | 8 |  |
| PVA-SbQ-propional | 8 | 8 |  | — |
| Bis-cetearyl dimethicone |  | 1.5 |  |  |
| Dimethicone |  | 1.5 |  |  |
| Water qs | 100 | 100 | 100 | 100 |

*partially saponified polyvinylacetate polymer bearing stilbazolium groups, adsorbed on polyvinylacetate particles (15% of dry extract).

Composition A according to the invention was applied to fine, short hair at 2 to 4 g of composition per half head. The hair treated was irradiated under UVA at 365 nm for an energy of 8 J/cm$^2$.

After the application and after 1 and 5 washes with shampoo, provision of style and cosmetic was observed. In particular, a clear provision of style, volume, density and body is observed up to 5 washes with shampoo.

Compositions A and C were also applied to tresses of wet natural hair with 90% grey hair, that were dried then irradiated under UVA at 365 nm for an energy of 8 J/cm$^2$. The tresses were then treated with a dye composition obtained from a solution that comprises:

0.4668 g of RED 80 colorant (SIRIUS ROT F3B-Bayer),
0.125 ml of pure acetic acid, and
water qs 100 ml.

This solution is diluted 5 times to obtain the dye composition.

The tresses treated are washed 10 times with shampoo.

A Datacolor Spectra Flash SF600X spectrophotometer was used to evaluate variation in tress colour.

Colorant "red 80", which has an affinity with the polymer, allows evaluation of the quantity of polymer remaining after several washes with shampoo.

The colour of tresses was evaluated before and after washing, in the L*a*b* system. In this L*a*b* system, the three parameters denote, respectively, the intensity (L*), a* indicates the green/red colour axis and b* the blue/yellow colour axis.

The variation in the tress colour before and after washes is measured ($\Delta E$) according to the following equation:

$$\Delta E = \sqrt{(L^* - L_o^*)^2 + (a^* - a_o^*)^2 + (b - b_o^*)^2}$$

In this equation, L*, a* and b* represent the values measured after washing and L0*, a0* and b0* represent the values measured before washing.

The larger the value of $\Delta E$, the greater the difference in colour before and after washing operations, and in the present case, the less persistent the film is.

The results are reported in the table below.

|  | T0 | After 5 washes with shampoo | After 10 washes with shampoo |
|---|---|---|---|
| C (comparative) | $L^* = 40.3$ $a^* = 33.6$ $b^* = 13.8$ | $\Delta E = 20.8$ | $\Delta E = 23.5$ |
| A (Invention 1) | $L^* = 40.8$ $a^* = 33.9$ $b^* = 15.0$ | $\Delta E = 5.7$ | $\Delta E = 10.0$ |

These results show an improvement in persistence of the sleeve after 10 washes with shampoo with the composition of the invention compared with the comparative composition that contains a PVA-SbQ polymer without a hydrophobic group.

Example 3

The following compositions were made in inverse emulsion form (quantity in % weight of active ingredient)

|  | D | E | F | G | C1 (Comparative) |
|---|---|---|---|---|---|
| PVA-SbQ* | — | — | — | — | 2 |
| Propyl-PVA-SbQ | 2 | — | — | — | — |
| Butyl-PVA-SbQ | — | 2 | — | — | — |
| Hexyl-PVA-SbQ | — | — | 2 | — | — |
| Octyl-PVA-SbQ | — | — | — | 2 | — |
| Water | Qs 100 | Qs 100 | Qs 100 | Qs 100 | Qs 100 |

*partially saponified polyvinylacetate polymer bearing stilbazolium groups, adsorbed on polyvinylacetate particles (15% of dry extract).

Compositions D to F according to the invention and C1 were also applied to to tresses of wet natural hair with 90% grey hair, on the one hand, and on tresses of permanent hair, on the other hand, at the rate of 1.6 g of composition per gram of hair. These tresses were dried then irradiated under UVA at 365 nm for an energy of 8 J/cm². The tresses were then treated with a dye composition described in Example 2. The tresses thus treated were then subjected to 5 washings with shampoos.

As in Example 2, the variation in color of the tresses was evaluated by looking at the tresses before and after washes in the L*a*b* system.

An improvement in persistence of the sleeve after 5 washes with shampoo with compositions D to F of the invention compared with the comparative composition C1 that contains a PVA-SbQ polymer without a hydrophobic group was observed.

The invention claimed is:

1. A method for treating hair, comprising:
a) applying to the hair a composition comprising a photo-crosslinkable polymer, wherein the photo-crosslinkable polymer is:

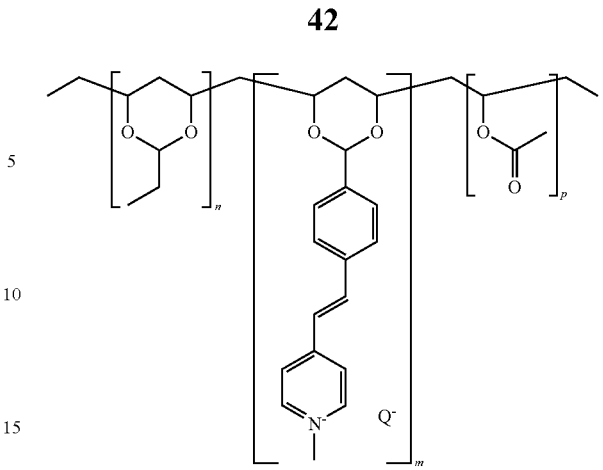

wherein:
Q⁻ is $CH_3OSO_{3-}$;
the total amount of the units bearing the stilbazolium pendent group, represented by m, ranges from 0.5% to 5%;
the total amount of the units bearing the alkyl group, represented by n, ranges from 2% to 20%; and
the total amount of the units bearing oxygen, represented by p, ranges from 5% to 97.5%;
wherein all percentages are by mole, based on the total amount of the photo-crosslinkable polymer; and
b) irradiating the composition on the hair to crosslink the polymer.

2. The method of claim 1, wherein the photo-crosslinkable polymer is soluble or dispersed in the composition.

3. The method of claim 1, wherein the photo-crosslinkable polymer is in the form of particles.

4. The method of claim 1, wherein the photo-crosslinkable polymer is present in an amount ranging from 0.01% to 25% by weight, relative to the total weight of the composition.

5. The method of claim 1, wherein the photo-crosslinkable polymer is present in an amount ranging from 1% to 15% by weight, relative to the total weight of the composition.

6. The method of claim 1, wherein the composition further comprises at least one solvent chosen from water, alcohols, polyols, polyol ethers, or mixtures thereof.

7. The method of claim 6, wherein the at least one solvent is present in an amount ranging from 0.1% to 99% by weight, relative to the total weight of the composition.

8. The method of claim 1, wherein the composition further comprises at least one fatty substance.

9. The method of claim 1, further comprising drying the hair, before the irradiation step and/or after the application step.

10. The method of claim 1, further comprising leaving the composition on the keratin substances for a period of time at room temperature, or under red light, before and/or after the irradiation step.

11. The method of claim 1, wherein the composition on the hair is irradiated with radiation in the UVA or the visible domain.

12. The method of claim 11, wherein the UVA radiation is between 250 nm and 400 nm.

* * * * *